(12) United States Patent
Murray

(10) Patent No.: US 7,485,467 B2
(45) Date of Patent: Feb. 3, 2009

(54) METHOD FOR MONITORING TEXTILE FIBER QUALITY, ANALYSIS AND IDENTIFICATION OF PAPER, WOOD, GRAINS, FOODS AND OTHER CELLULOSE CONTAINING MATERIALS USING GLYCAN OLIGOMER ANALYSIS

(75) Inventor: Allen K. Murray, Newport Beach, CA (US)

(73) Assignee: Glycozyme, Inc., Irvine, CA (US)

( * ) Notice: Subject to any disclaimer, the term of this patent is extended or adjusted under 35 U.S.C. 154(b) by 303 days.

(21) Appl. No.: 10/690,386

(22) Filed: Oct. 20, 2003

(65) Prior Publication Data

US 2004/0152201 A1     Aug. 5, 2004

(51) Int. Cl.
    *G01N 33/00*     (2006.01)
    *G01N 1/18*     (2006.01)
    *G01N 33/34*     (2006.01)
    *G01N 33/46*     (2006.01)

(52) U.S. Cl. .......................... 436/94; 436/87; 436/178; 73/53.03

(58) Field of Classification Search ................... 436/94, 436/87, 178; 73/53.03
See application file for complete search history.

(56) References Cited

OTHER PUBLICATIONS

Massiot, P. et al, Changes in cell-wall polysaccharides of ambarella fruit during juice extraction and clarification, Sciences des Aliments, vol. 11 No. 3 pp. 447-489 (1991).*

* cited by examiner

*Primary Examiner*—Jill Warden
*Assistant Examiner*—Keri A Moss
(74) *Attorney, Agent, or Firm*—Bozicevic, Field & Francis LLP; Connie C. Tong

(57) ABSTRACT

A method of analyzing cell wall components based on a hot dilute acid extraction, followed by alcohol precipitation, of plant cellulosic materials such as cotton fibers or wood pulp. The extracts are analyzed by high pH anion exchange chromatography to separate and characterize the carbohydrates. This method extracts a characteristic series of carbohydrate multimers containing galactose, mannose and glucose. The pattern of multimers is indicative of origin of the cellulosic material (e.g., the plant species the material comes from) as well as quality and processing state of the material. The alcohol precipitation improves the discriminating powers of the analysis so that the species of origin of plant products can be identified.

15 Claims, 39 Drawing Sheets

METHOD FOR MONITORING TEXTILE FIBER QUALITY, ANALYSIS AND IDENTIFICATION OF PAPER, WOOD, GRAINS, FOODS AND OTHER CELLULOSE CONTAINING MATERIALS USING GLYCAN OLIGOMER ANALYSIS

This is a continuation-in-part application of WO 02/086496 filed 20 Apr. 2001 designating the United States and claims priority from that application which is incorporated in here by reference.

1. Field of The Invention

This invention concerns a method of monitoring precursor pools for cell wall biosynthesis and using them to identify the origins of various plant cell walls. In particular this application describes biochemical methods of assessing the quality of cotton fibers and of "fingerprinting" wood samples, food grains, foods derived from plant materials and any other material derived from a plant source.

2. Description of Related Art

In earlier applications the present inventor described his surprising discovery that it is possible to extract a carbohydrate-containing fraction from properly prepared plant material by a simple cold water process. Essentially, plant tissue is prepared by rapid freezing (preferably by use of liquid nitrogen or solid carbon dioxide) and is then lyophilized and stored at temperatures below freezing. This inventor has shown earlier that carbohydrate-containing cell wall fractions can be easily extracted from the lyophilized tissue by cold aqueous extraction; then, special techniques of High Performance Liquid Chromatography (HPLC) allow resolution of the aqueous extract into constituent mono and polysaccharides which can be further hydrolyzed to identify the constituent monosaccharides.

The use of high pH anion exchange chromatography with pulsed amperometric detection (HPAEC-PAD) makes possible the unambiguous identification of cell wall constituents. In HPAEC a salt gradient (such as a sodium acetate gradient) is applied to a column of special ion exchange resins held at a high pH to sequentially elute various mono and polysaccharides. Essentially, the hydroxyl groups of the sugars act as extremely weak acids that become deprotonated at the high pH, binding to the ion exchange matrix until eluted by the gradient.

While there are a number of vendors of HPAEC materials, the current invention has employed products and systems produced by the Dionex Corporation of Sunnyvale, Calif. These products and systems are explained in full in the Dionex Technical Notes, particularly in Technical Notes 20 and 21, which are hereby incorporated into this application. The carbohydrate fractions isolated from plant cell walls were analyzed using Dionex CarboPac PA1 and PA-100 columns. Both of these columns contain polystyrene/divinylbenzene cross-linked latex microbeads (350 nm diameter) with quaternary amine functional groups. The columns were operated under the manufacturer's recommended pressure conditions (4000 psi maximum) in sodium hydroxide eluted with a sodium acetate elution gradient. When necessary, sugar alcohols were analyzed using a CarboPac MA1 column that contains porous beads (8.5 μm diameter) of vinylbenzene chloride/divinylbenzene with alkyl quaternary ammonium functional groups The polysaccharides analyzed in the present invention are appropriately referred to as "glycoconjugates" because they comprise a monosaccharide conjugated to an additional monosaccharide (i.e., to form an oligo or polysaccharide) or sugar alcohol and optionally to a protein or a lipid. As will be disclosed below, at least some of the glycoconjugates comprise polysaccharides conjugated to a protein moiety. To summarize, glycoconjugates may be polysaccharides, polysaccharides containing a protein moiety, polysaccharides containing a lipid moiety and/or any combination of these. In the present application only polysaccharides and polysaccharides containing a protein moiety have been unambiguously identified. In any case HPAEC characterizes the polysaccharide component of the glycoconjugate.

SUMMARY OF THE INVENTION

Not only are oligosaccharides and oligomers (multimers) found in extracts of fibers sampled directly from cotton bolls, but extracts of cotton textiles produce peaks having the same retention times, relative to known compounds, as do the extracts of fibers from plant material. Moreover, the same oligosaccharides and oligomers can be recovered from cotton textiles, e.g. denim, sheets and towels after prolonged wear and washings. The effect of washing is to reduce the quantity of the oligosaccharides and oligomers extracted, relative to those found in newly-manufactured textile products or cotton fibers sampled from bolls.

Similar oligosaccharides and oligomers may also be extracted from woods. Twenty-two different woods have been extracted. While many of the same oligosaccharides and oligomers are found in the woods and in cotton, no two species of wood have been found to be display identical chromatograms. Thus each species of wood has a distinct signature. For example, birch and pine vary in peaks eluting between approximately 15 and 20 minutes; while balsa, a very low density wood has lower levels overall. As with the new and old cotton products, there appears to be an effect of washing and aging with woods as well. Chromatograms of teak that has been part of the deck of a sea-going vessel for nineteen years are almost indistinguishable from those of recently-harvested teak, except that the scale of the weathered teak must be expanded 4× for the chromatograms to appear congruent. For both cotton and wood, a probable hypothesis is that fractions of oligosaccharides and oligomers have leached out of the cell wall constituents with successive exposure to water and salts. Loss of the oligosaccharides and oligomers may indicate, and may in fact constitute, wear and loss of integrity of the fabric and wood fibers.

Various paper products also display oligosaccharides and oligomers similar to those found in cotton and wood. As with woods, every paper product tested to date has produced a unique chromatogram. Whereas the differences among the woods are probably due to differences in biochemistry and patterns of growth, the differences among the paper products illustrate differences in both cellulose source and in processing, such as type and degree of bleaching, coloring, and surface finishing, etc.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide methods for determining identity and quality of plant cell wall materials, especially cotton fibers, and other cellulose containing products, such as wood and paper, through the analysis of selected polysaccharide fractions.

Cell wall biosynthesis is a highly complex process which involves soluble substrates being converted to insoluble products at the surface of the cell membrane or external to it. This is complicated by the synthesis of a primary wall followed by the synthesis of the secondary wall often with overlap of the synthesis of both. The products include polysaccharides, glycoproteins, proteins and enzymes which may exist in complexes or be covalently linked to each other. Correlations between cell growth and substrate concentrations and the activities of several enzymes have been made (Murray and Bandurski, 1975; Murray and Brown, 1997). The fact that hydrolysis of sucrose to glucose and fructose is an integral part of fiber wall synthesis (Basra et. al., 1990) is consistent with findings described in the instant application. A direct relationship between cell growth and acid invertase activity has been demonstrated in several plant tissues (Morris and Arthur, 1985; Sturm and Chrispeels, 1990; Basra et. al., 1990; Sturm, et. al., 1995; Buchala, 1987). The increased invertase activity. is the result of transcription of messenger RNA, rather than simply an enzyme kinetic effect, therefore, the invertase response is specific and induced (Sturm and Chrispeels, 1990; Sturm, et. al., 1995).

The secondary cell wall of cotton fibers consists almost entirely of cellulose which directs interest to cellulose biosynthesis. The potential role of sucrose synthase with the cellulose synthetic apparatus has been proposed (Amor, et. al., 1995, Delmer, 1999). The possible role of the invertase mentioned above, the possible role of lipid-bound intermediates (Matthyse, et. al., 1995; Brett, 2000) and the suggestion of self-assembly mechanisms (Brett, 2000) remain observations in search of explanations. In this specification I describe a series of glycan oligomers which appear to be associated with this cell wall biosynthetic process.

Figure 1:
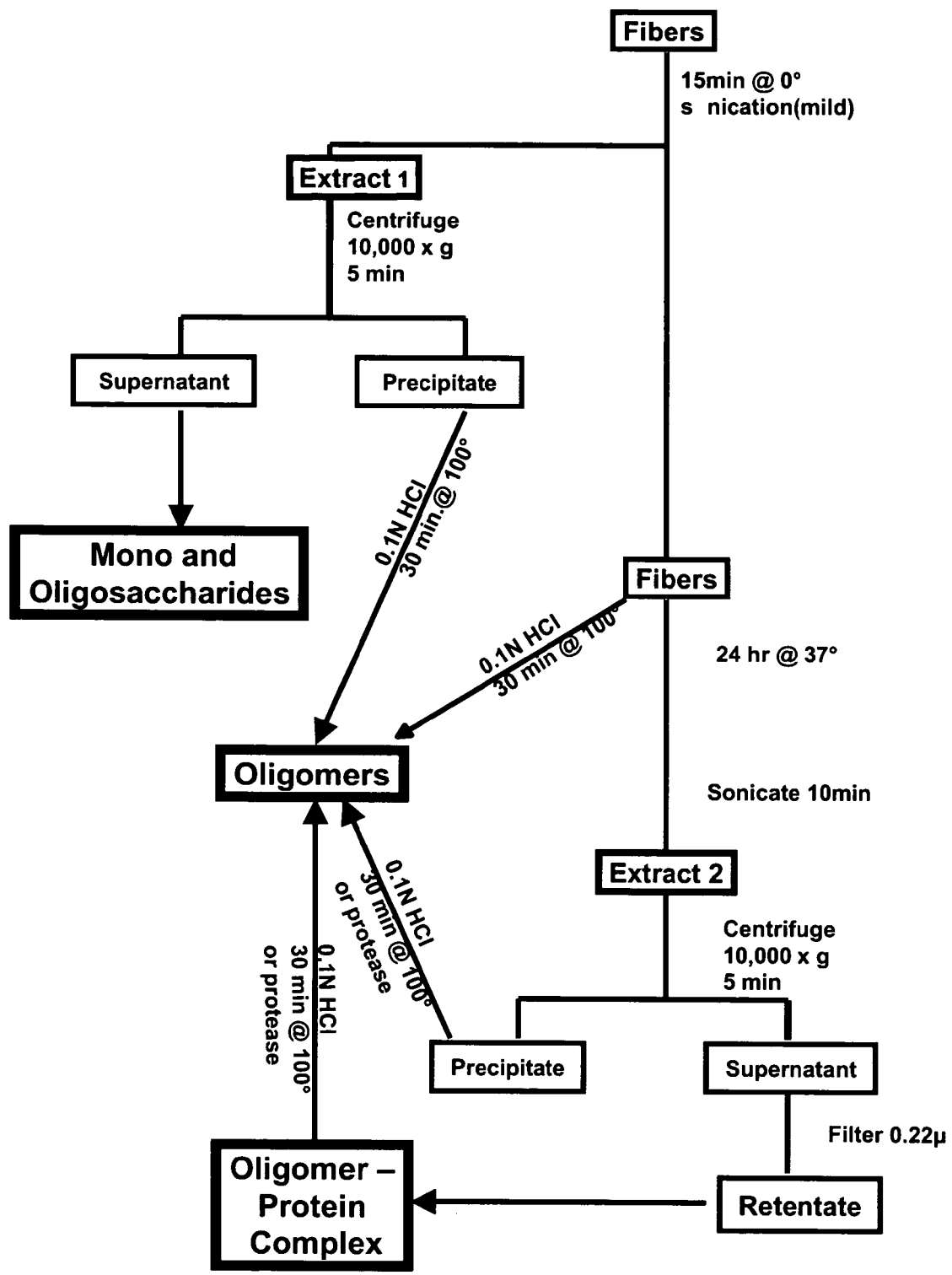
FIG. 1 shows a flow diagram for the isolation of the oligomers from cotton fibers; other plant source materials used were extracted following the top left branch of the diagram.

The period of cotton lint development, from pollination to dry, mature fiber extends only about 45 days. The rates of cellulose deposition, on a per mm fiber length basis, vary with one maximum at 16 days post anthesis (DPA) and a greater maximum at 28 DPA (Meinert and Delmer, 1977). Prior to 21 DPA well defined fibers are usually not present in developing bolls. However, only after the first 21 days have elapsed, can fibers be excised from developing bolls. A practical way to investigate fiber development is to freeze bolls in the field, and subsequently lyophilize them. Fractionation of the rehydrated, developing fibers yields mono- and oligosaccharides, oligomers, an oligomer-protein complex, as well as insoluble fiber material as shown in FIG. 1.

The several carbohydrates and the carbohydrate-protein complexes vary in a manner that is consistent with known characteristics of cell wall development in plants. I have identified a series of glucose containing oligomers, which are ubiquitous in all plant tissues investigated to date including monocots, dicots, and marine algae. The quantitative distribution and presence of specific oligomers appears to be unique to each plant and tissue as well as to the developmental stage. The oligomers can be extracted using weak acid from developing cotton fibers, mature cotton fibers, cotton dust and cotton fabric at various stages of processing as well as from old fabric, paper and wood.

My interest is in understanding the dynamics of carbohydrate metabolism during cotton fiber development. Since a plant cell must synthesize cell wall material in order to grow and develop, knowledge of the events in cell wall biosynthesis can be used to monitor plant growth and to detect aberrations in growth due to environmental influences (Murray, 1998, 2000). The cotton fiber is unique in its development since it is a plant cell that usually does not divide or store starch. During the period of fiber elongation, it is generally synthesizing primary cell wall (Graves and Stewart, 1988). Following the period of cell elongation, the fiber cell thickens as it synthesizes secondary cell wall, which consists almost entirely of cellulose.

The glycans described below constitute another piece of the cell wall biosynthetic process. Since they can be extracted from developing cotton fibers, mature cotton fibers and aging cotton fibers in fabric, they may be subunits of the cotton fiber. Since they have been extracted from every sample of plant cell wall material examined suggests that they are fundamental elements, which occur with cellulose.

Figure 38:
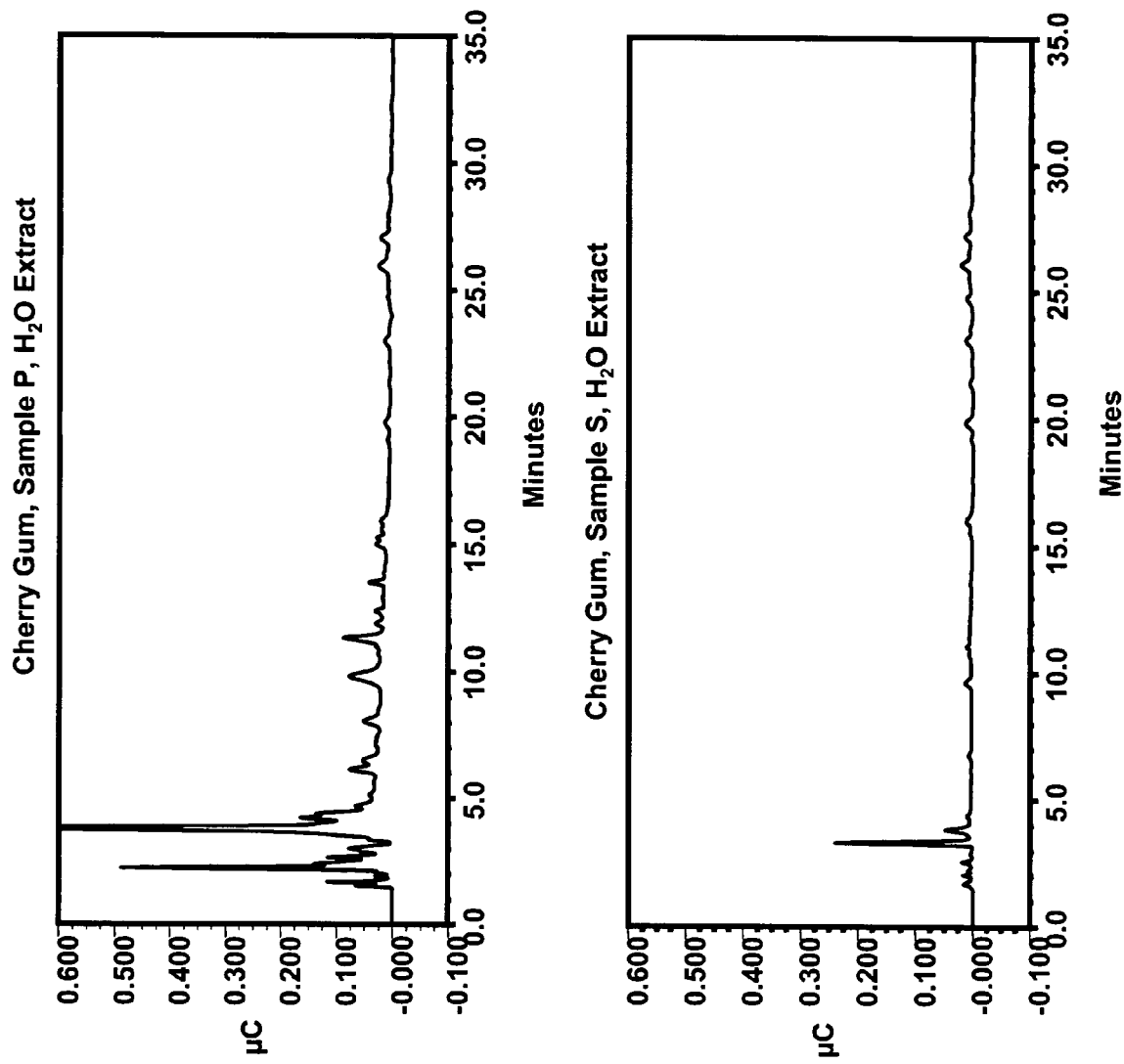
FIG. 38 shows the carbohydrate profiles for water extracts of Cherry gums from two different sources.
Figure 39:
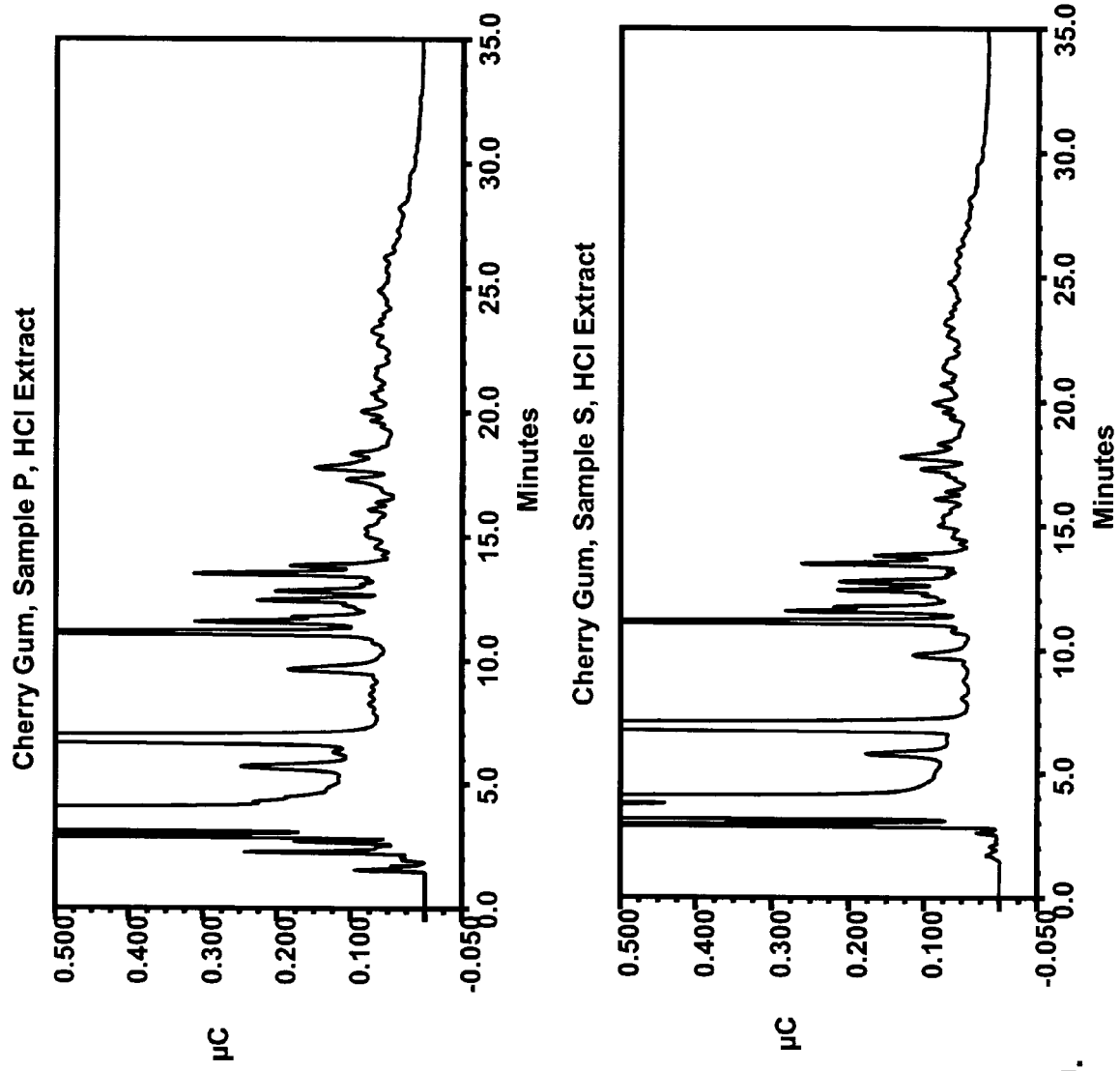
FIG. 39 shows the carbohydrate profiles for the HCl extracts of Cherry gums from two different sources.

Not only are the oligomer profiles of each source of plant material unique but the exudate gums from different species are also unique. Both the aqueous extracts and the HCl extracts are unique. As shown in FIGS. 38 and 39 note that the HCl extracts are similar while the water extracts are determinative. This method is ideally suited to identify foods for sources of plant gum additives. Also, it has been discovered that varnishes, vehicles, adhesives and materials used in paintings and various fine art works contain unique plant gum "signatures" that can be identified with the inventive method. It is essentially impossible to duplicate the patterns found in old painting or other art works so that the current method is an ideal means to identify paintings or other works of art. This can be achieved using only a few milligrams of material.

Figure 31:
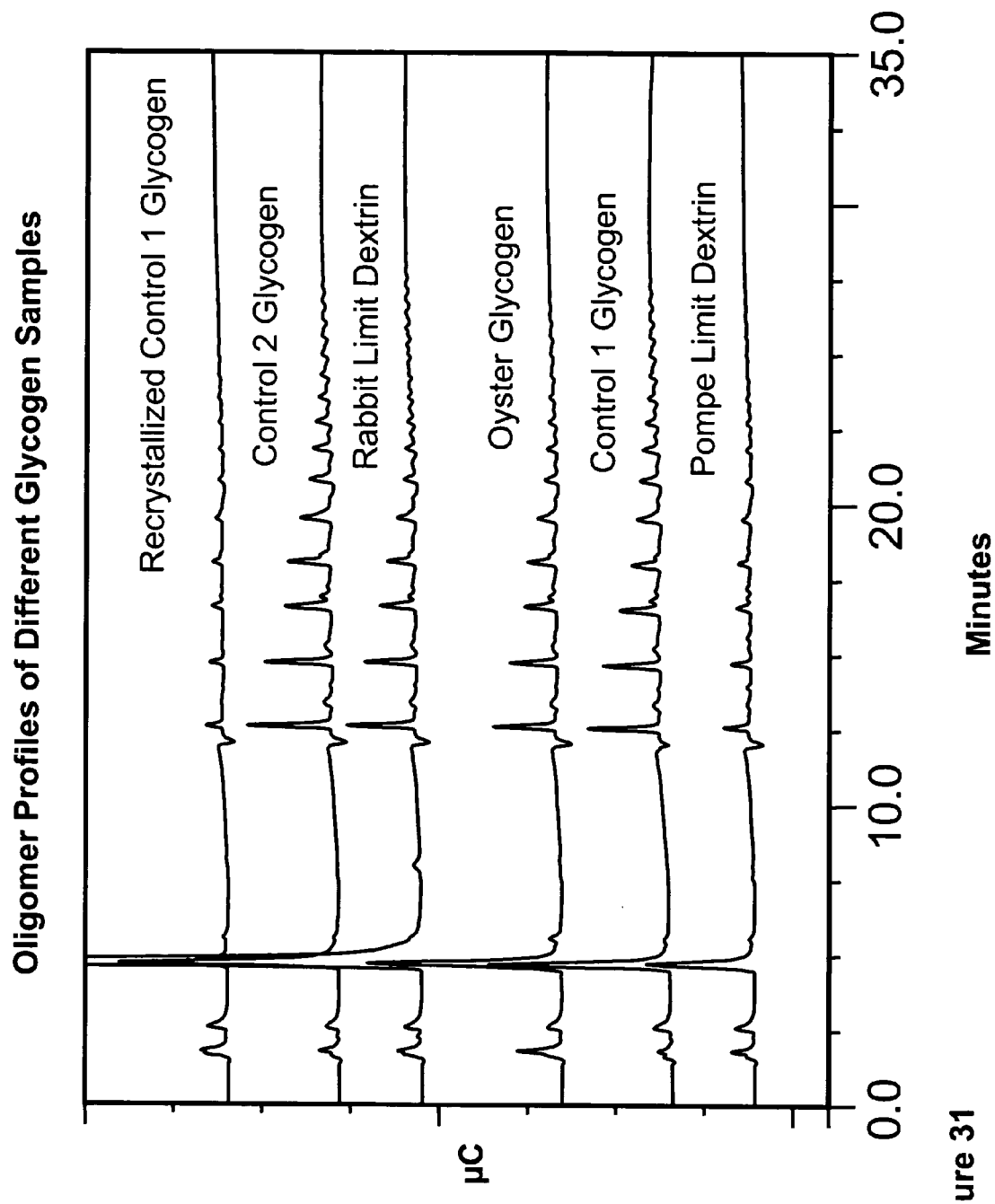
FIG. 31 shows the oligomer profiles of different glycogen samples.
Figure 32:
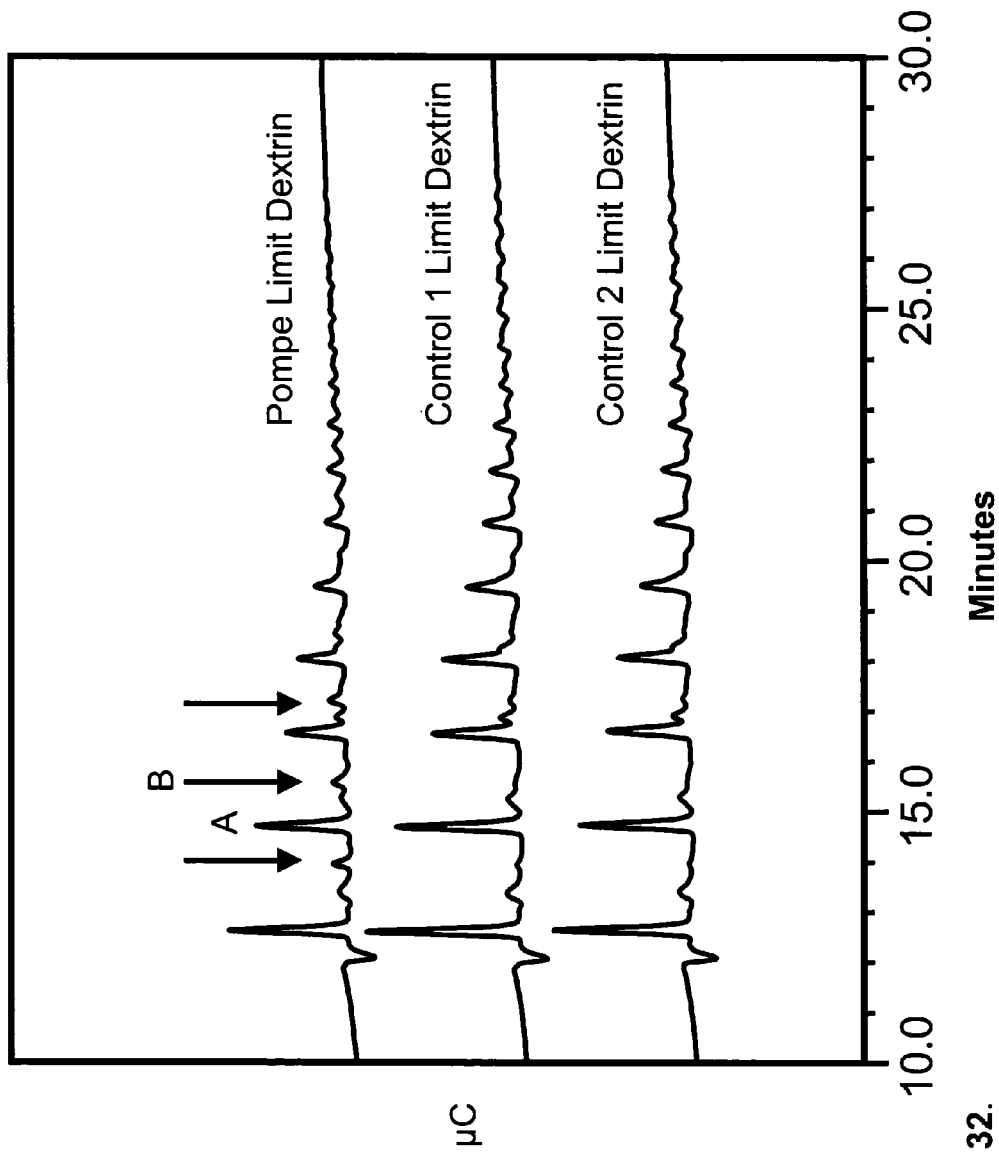
FIG. 32 show the oligomers extracted from limit dextran samples from both control human liver samples and the one from the patient with Pompe disease.

The glycan oligomers were detected in all samples of glycogen studied as shown in FIG. 31. The elution profiles are very similar to those of cellulosic substances. The profile of the oligomers released from the glycogen from the liver of a patient with Pompe disease did display three minor peaks which are either not present or are present in much lesser quantities. These three peaks were higher than the immediately preceding minor peak but in all other glycogen samples they were present in a lesser amount than the immediately preceding peak as shown in FIG. 32. Three vertical arrows indicate the three peaks.

Figure 33:
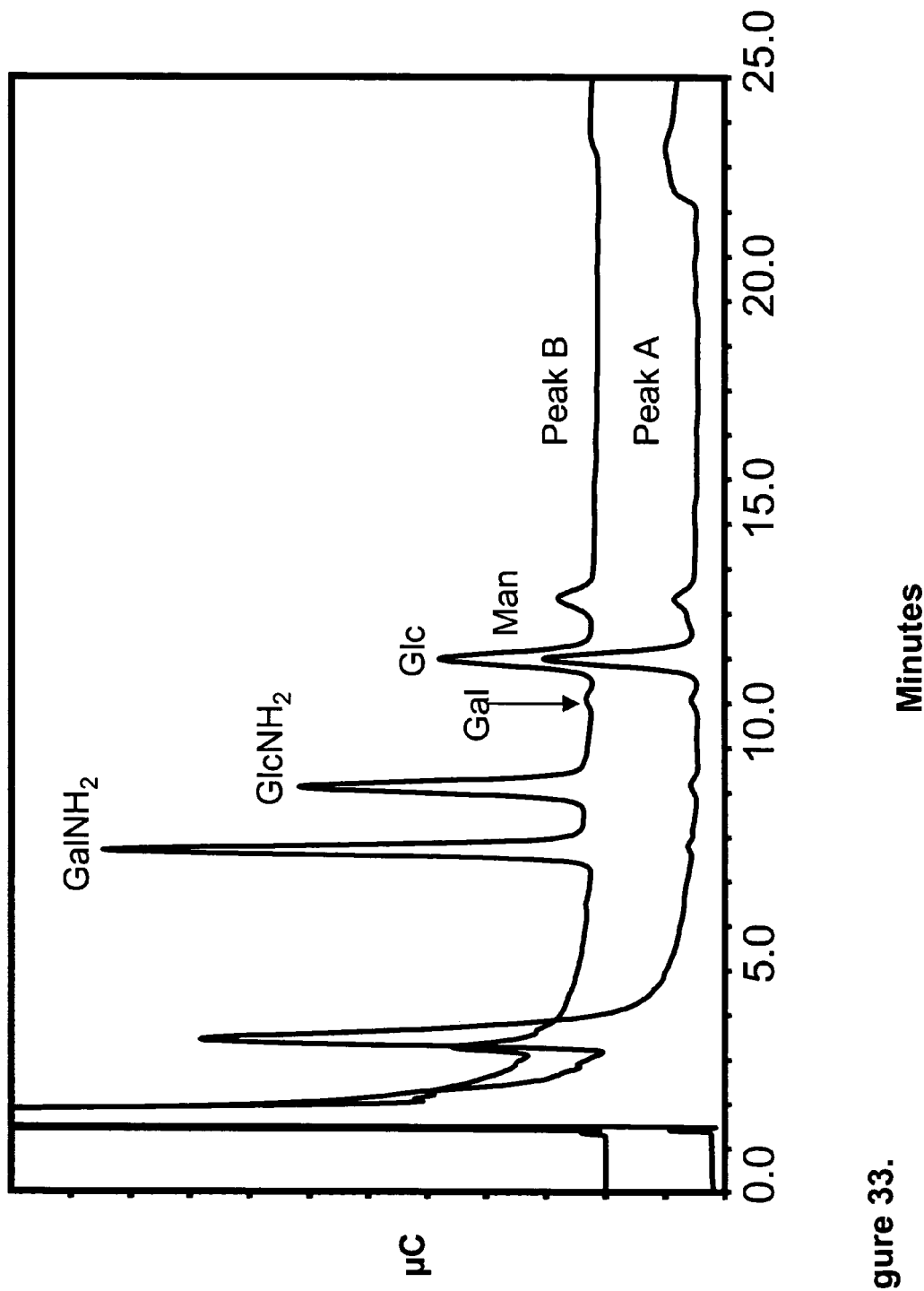
FIG. 33 shows the monosaccharide profiles of peaks A and B isolated from the Pompe limit dextran shown in FIG. 32.
Figure 34:
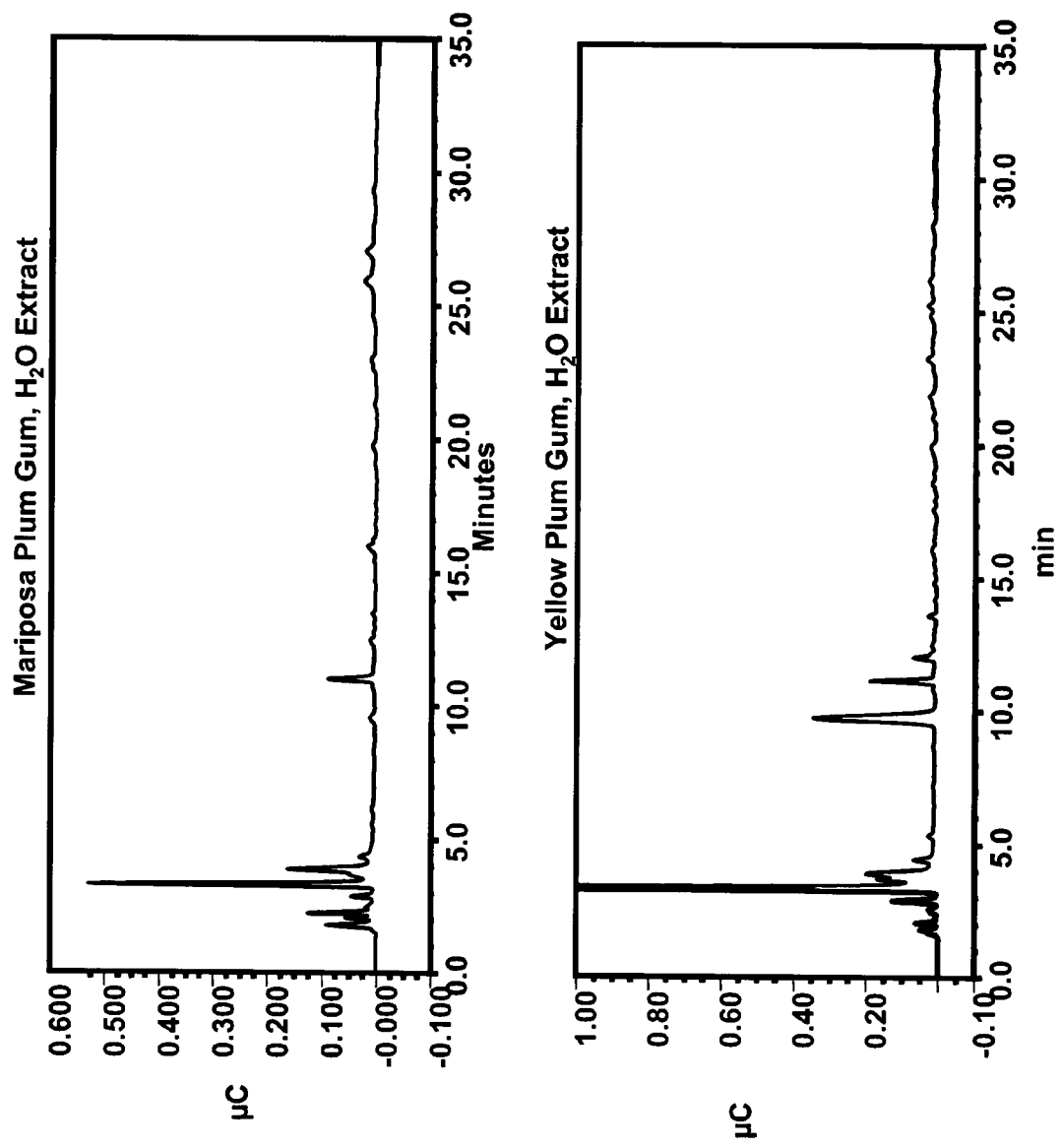
FIG. 34 shows the carbohydrate profiles for water extracts of Plum gums from two different sources.
Figure 35:
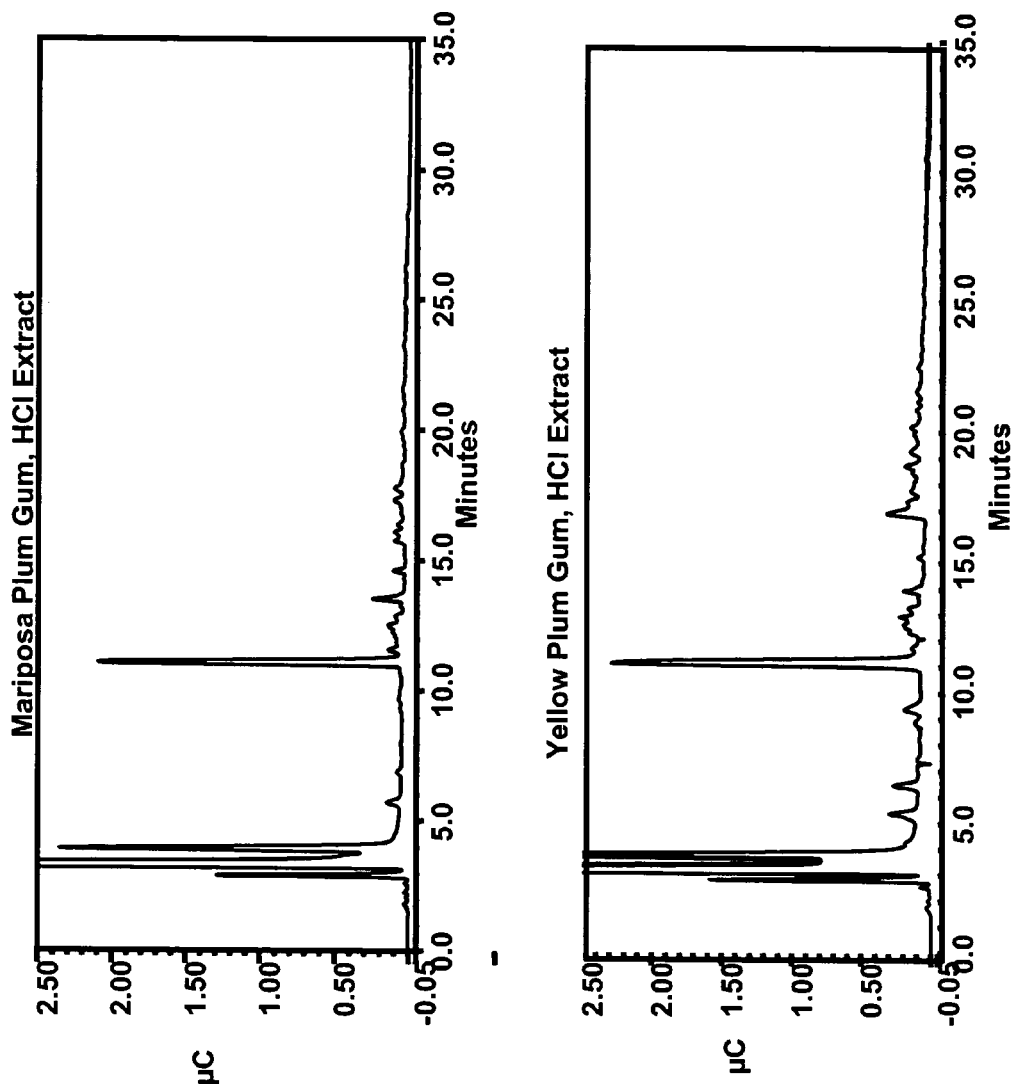
FIG. 35 shows the carbohydrate profiles for the HCl extracts of Plum gums from two different sources.
Figure 36:
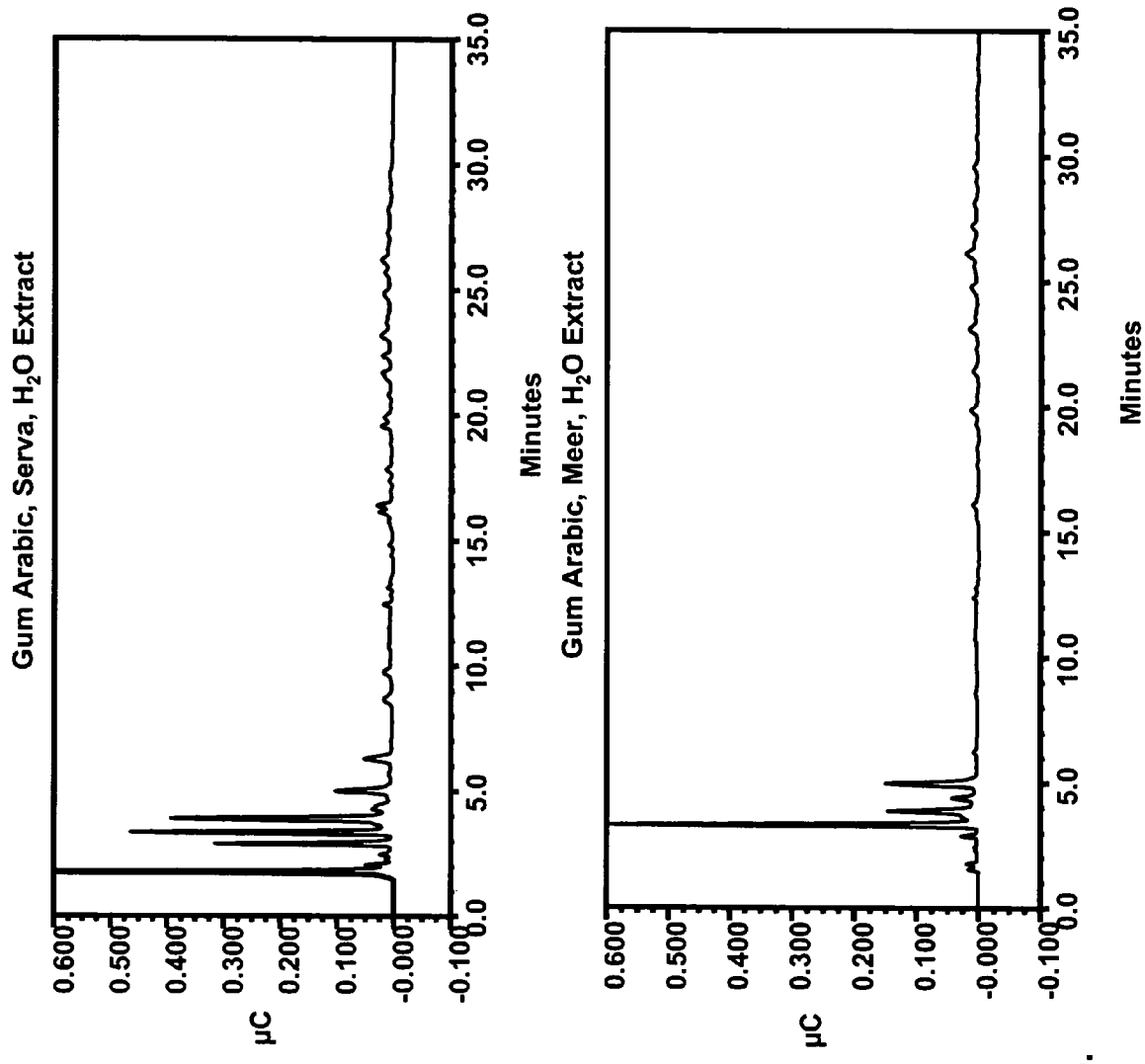
FIG. 36 shows the carbohydrate profiles for water extracts of Gum Arabic from two different sources.
Figure 37:
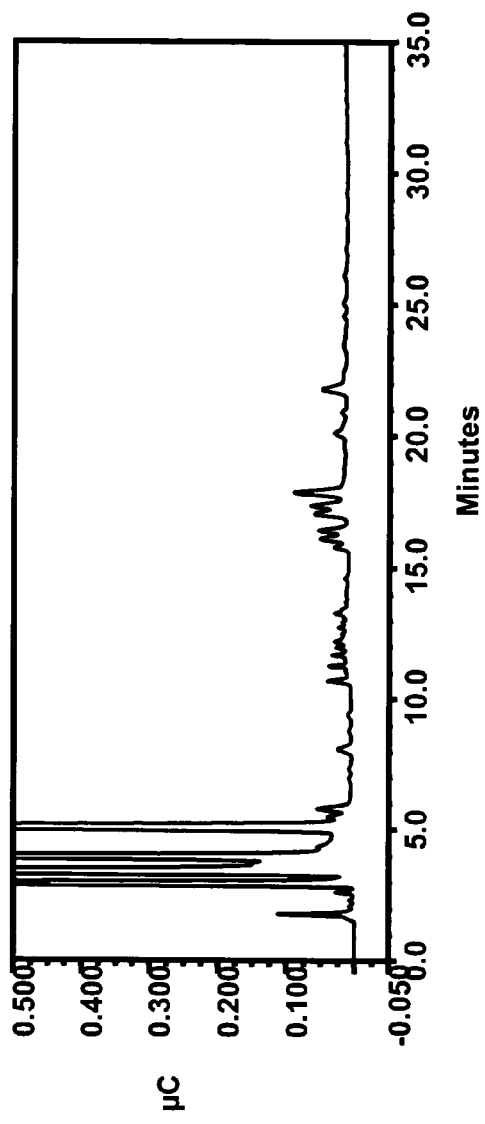
FIG. 37 shows the carbohydrate profiles for the HCl extracts of Gum Arabic from two different sources.
Figure 37:
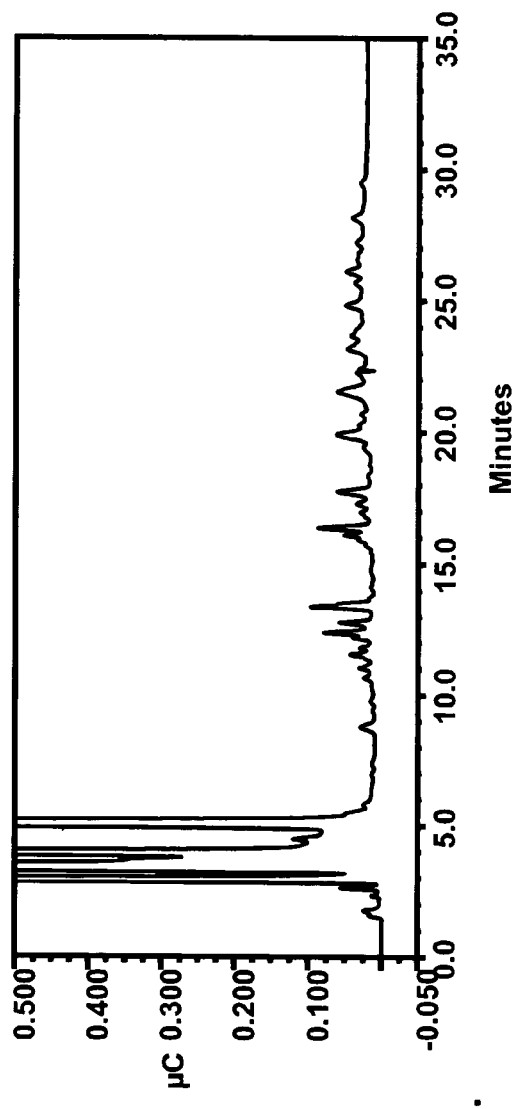

One of these peaks of interest and its preceding major peak labeled as b and a respectively in FIG. 32 were collected and the material was hydrolyzed to determine the monosaccharide composition. The monosaccharides released from these two peaks are shown in FIG. 33. Both peaks contain galactosamine, glucosoamine, galactose, glucose and mannose however the relative content of galactosamine and glucosamine was much greater in peak b than in peak a. In addition, there is a small shoulder on the leading edge of the mannose peak in the hydrolyzate from sample a may be xylose but this will require additional investigation.

Materials and Methods

Plant material. Cotton, *Gossypium hirsutum* var. DP-50, was grown in the Mississippi Delta region for the time of day samples which were collected at 7 am, noon and 7 pm at 25

DPA. Plants used for the sequential boll experiments were also *G. hirsutum* var. DP-50 but were grown in the Sacramento Valley of California. Sequential bolls were taken at the same time from the same plant. Bolls were placed on ice and frozen on dry ice as soon as possible following collection.

Extraction of fibers. The lyophilized fibers were first extracted with water at 0° to remove soluble oligosaccharides and monosaccharides (Murray, 1998). Typically, a 20 mg sample of fibers was placed in a 1.7 ml screw cap plastic tube to which 0.5 ml water was added, the tube shaken, then placed in a Branson 85 W sonicator filled with ice water. Following removal of the cold water extract with a Pasteur pipette, 0.5 ml of 0.1N HCl was added and the tube was placed in a boiling water bath for 30 minutes to extract the glucose containing oliogmers (Murray, 2000). The mono- and oligosaccharides extracted by the cold water procedure include myo-inositol, galactinol, arabinose, glucose, fructose, melibiose, sucrose, manninotriose, verbascotetraose, raffmose, stachyose, verbascose and, tentatively, ajugose which can be used as indicators of fiber development (Murray, 1998, 2000). The oligosaccharides extracted by the 0.1N HCl procedure can also be used as indicators of cell wall biosynthesis and fiber development (Murray, 2000). The HCl extracts were neutralized with an equivalent amount of 1N NaOH prior to HPAEC-PAD. In the case of fabric, wood, grain or paper products typically 40-60 mg of material was extracted in a volume of 1.0 ml.

Isolation of oligomer-protein colloid. To obtain the oligomer-protein colloid, the cold water extract was removed and 0.5 ml of water was added, with 50 µl of toluene layered on top to prevent microbial growth, the cap was screwed on tightly and the tube was placed in a 37° water bath for 24 hours. Following the incubation, the oligomer-protein colloid was isolated by first centrifugation at 15,000×g for 5 minutes after which the supernatant was filtered through a 0.22µ Z-Spin filter (Gelman) with the oligomer-protein colloid being retained by the filter. The oligomers were released from the oligomer-protein colloid by either chymotrypsin or by the weak acid extraction.

Alcolol Precipitation. The HCl extracts were neutralized with 1N NaOH prior to HPAEC-PAD. Alcohol precipitations were performed using ethanol or n-propanol. In each case, the neutralized HCl extract was made up to 80% ethanol or propanol. The preciptate formed immediately and was collected by centrifugation at 8000×g for 10 minutes and designated P1. The alcoholic supernatant was then put in a freezer at −80° C. overnight (16 hr) and recentrifuged to yield a second, less abundant, precipitate designated P2.

Figure 30:
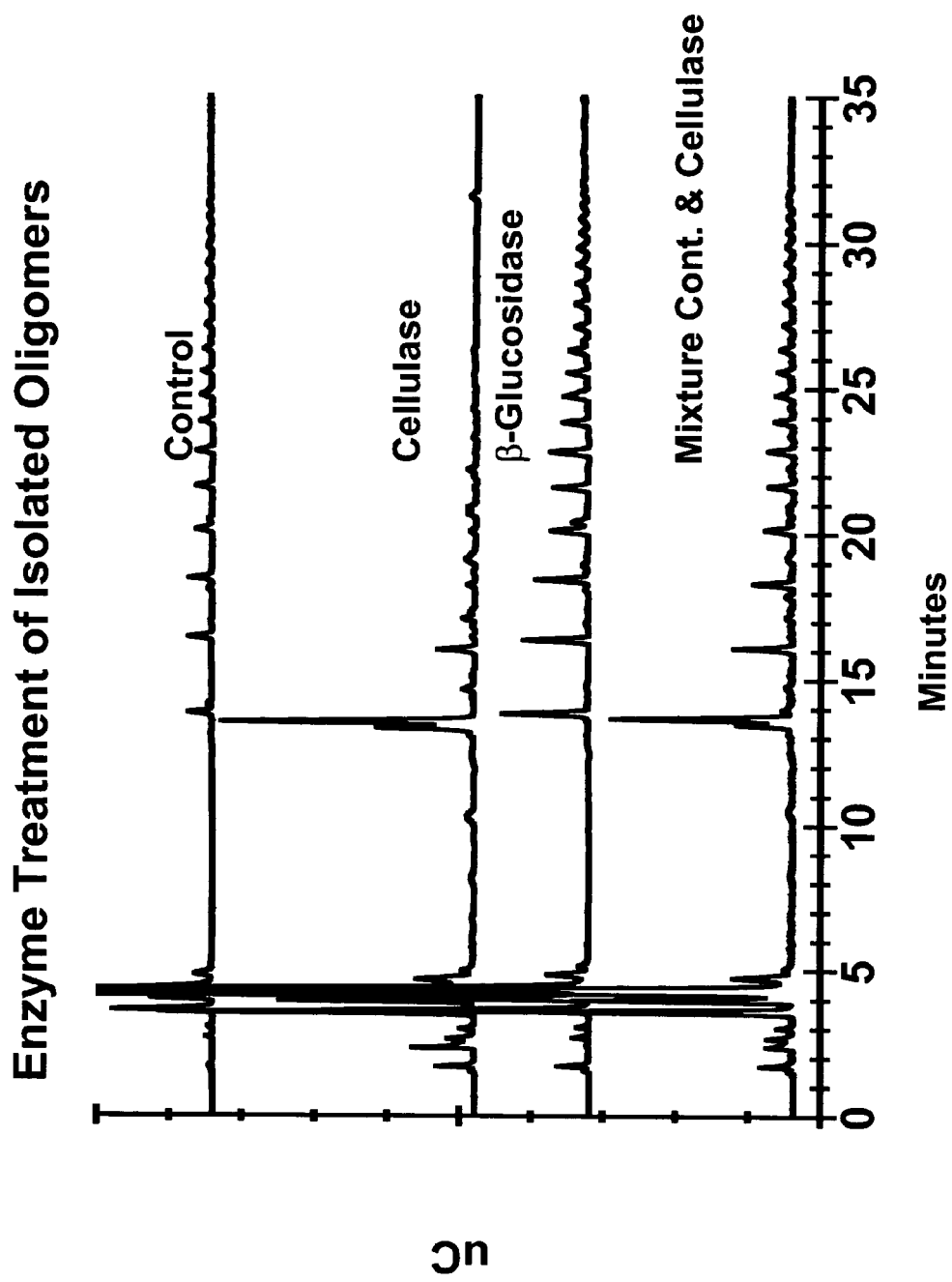
FIG. 30 shows oligomers (multimers) following treatment with cellulase or β-glucosidase and the control without treatment; the bottom plot shows a mixture of equal parts of the samples from the control oligomers and those treated with cellulase to determine if there were shifts in retention time of any of the peaks.

Enzyme Treatments. Extracted multimers were subjected to incubation with a cellulase (*Trichoderma reesei*) or a β-glucosidase (almond emulsin) both obtained from Sigma Chemical Company. The enzymes were used at a concentration of 1 mg/ml in 50 mM sodium acetate buffer, pH. 4.8. The effect of the β-glucosidase appeared to be to increase the heights of the multimer peaks significantly and to generate one additional small peak with a retention time slightly greater than 20 min. Presumably this is the result of removing terminal glucose unit(s) that results in a compound with an increased detector response. The cellulase gave a very different result since it resulted in the near elimination of many peaks and great reductions in many peak heights with a great increase in the peak height of the first peak in the series of multimers as shown in FIG. 30. Protease treatments of the carbohydrate-protein colloid were performed using a protein concentration of 1 mg/ml in water.

Collection of Human Tissue. Livers from an 18-month-old female with Pompe's disease and from two adult male accident victims were obtained at autopsy. The Pompe's liver (α-1,4-, α-1,6-glucosidase deficiency) and the first control liver (designated "Control 1") were obtained several hours post mortem at autopsy. In the case of the second control (designated "Control 2"), the patient was an organ donor, and the liver was obtained immediately. All tissue was stored at −76° C.

Isolation of Glycogen. Oyster and rabbit liver glycogen were obtained from Sigma Chemical Company. Human liver glycogen was isolated using a slight modification of the method of Mordoh et al. (1966) was used. Frozen liver was broken into pieces with a chisel and placed in the homogenizing medium at 4°. The pieces of liver were homogenized in 14 volumes of cold 0.11 M mercuric chloride which was adjusted to pH 5.0 with 1N sodium hydroxide. The Pompe's and Control 1 liver homogenates were subjected to five freeze-thaw steps, in an attempt to ensure rupture of the lysosomes and release of the stored materials.

The homogenate was centrifuged at 370×g for 5 minutes at 4°. Five volumes of 95% ethanol at 4° were added to the supernatant to precipitate the polysaccharide. me suspension was centrifuged at 1130×g for 10 minutes. The precipitate was dissolved in 1 to 3 volumes of water. 5 volumes of ethanol at 4° were added and the suspension was recentrifuged at 1130×g for 10 minutes. The precipitate was washed twice in 5 volumes of ethanol, and once in 5 volumes of acetone. The glycogen was then collected by suction filtration, dried in vacuo, and stored under desiccation at −20° C.

Preparation of Phosphorylase Limit Dextrin. Glycogen was treated with phosphorylase A to obtain an α-limit dextrin. (Illingworth et al., 1952). The various sources of glycogen were made up in water at a concentration of 1 mg/ml. The glycan oligomers were released by the method of Murray (2000). An equal volume of 0.2 n HCl was added to reach a final volume of 0.1 n HCl and the solutions were boiled for 30 minutes prior to neutralization.

Chromatography. HPAEC-PAD was performed using a CarboPac PA-1 column. The eluent was 150 mM sodium hydroxide, isocratic from 0 to 5 min then a linear sodium acetate gradient from 5 min to 40 min going from 0 to 500 mM in 150 mM NaOH at a flow rate of 1 ml/min. The detector wave form was the following: 0-0.50 sec, 0.1 V; 0.51-0.59 sec, 0.6 V; 0.60-0.65 sec, −0.6 V; integration 0.30-0.50 sec. For monosaccharide composition, oliogomers were obtained by collecting -fractions of the HPAEC-PAD eluent, which was passed through a Dionex ASRS-II anion suppressor to remove salt. Fractions were then lyophilized and taken up in 200 µl of water, made up to 2N trifluoroacetic acid (TFA) (Manzi and Varki, 1993). flushed with argon and sealed in screw cap plastic vials with O-rings. The samples were then placed in a heating block at 100° for 2-4 hr. Following hydrolysis, the samples were taken to dryness in a Speed-Vac overnight and then taken up in 200 µl of water for HPAEC-PAD on a Dionex CarboPac-PA10 column under isocratic conditions in 15 mM NaOH.

Acid Extractable Multimers.

Figure 20:
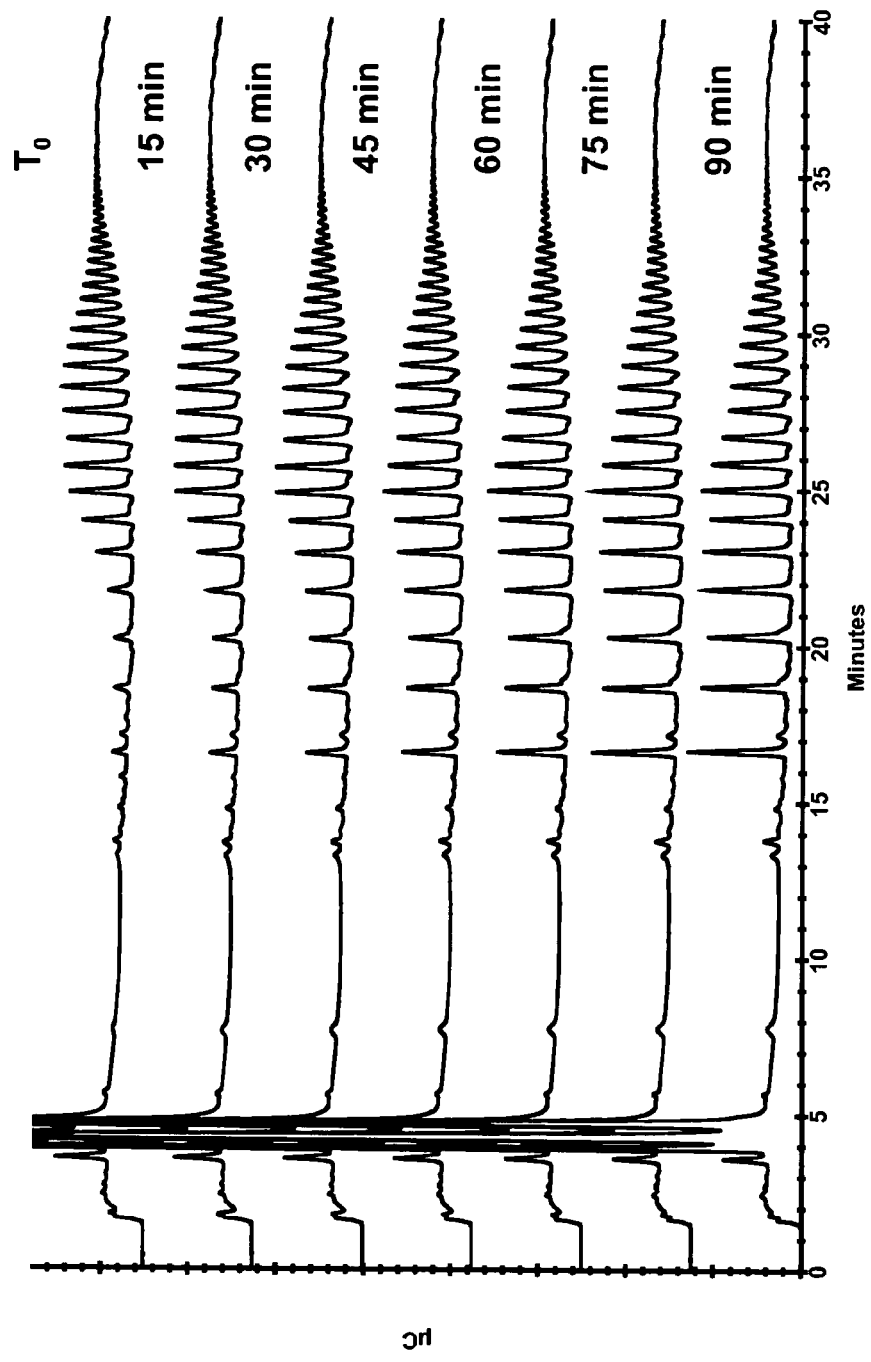
FIG. 20 shows propanol precipitates treated with cellulase for up to 90 min which results in a shift to earlier peak elution.
Figure 21:
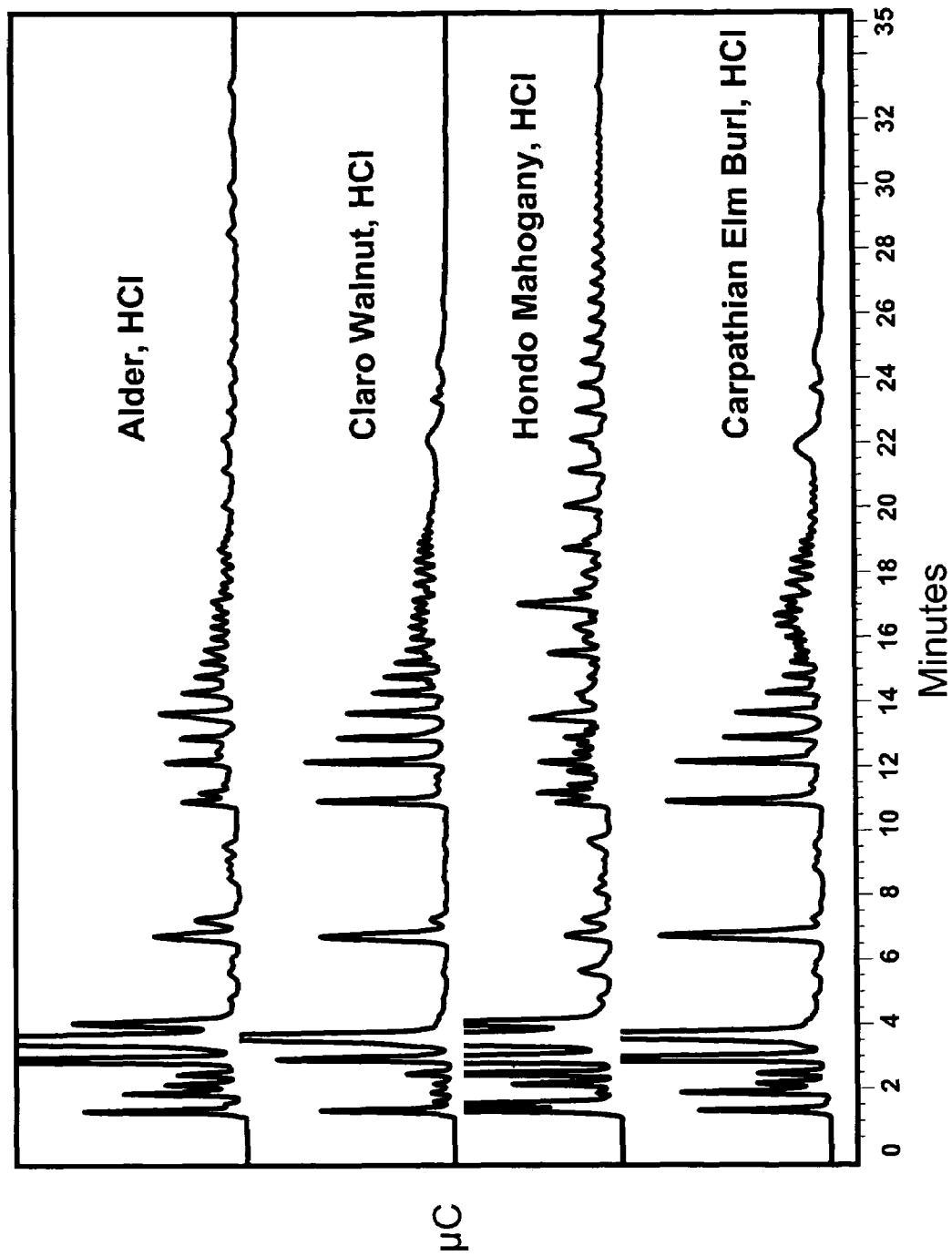
FIG. 21 shows the HCl extracts from four species of wood: a) alder; b) Claro walnut; c) Honduras mahogany and d) Carpathian elm burl.
Figure 22:
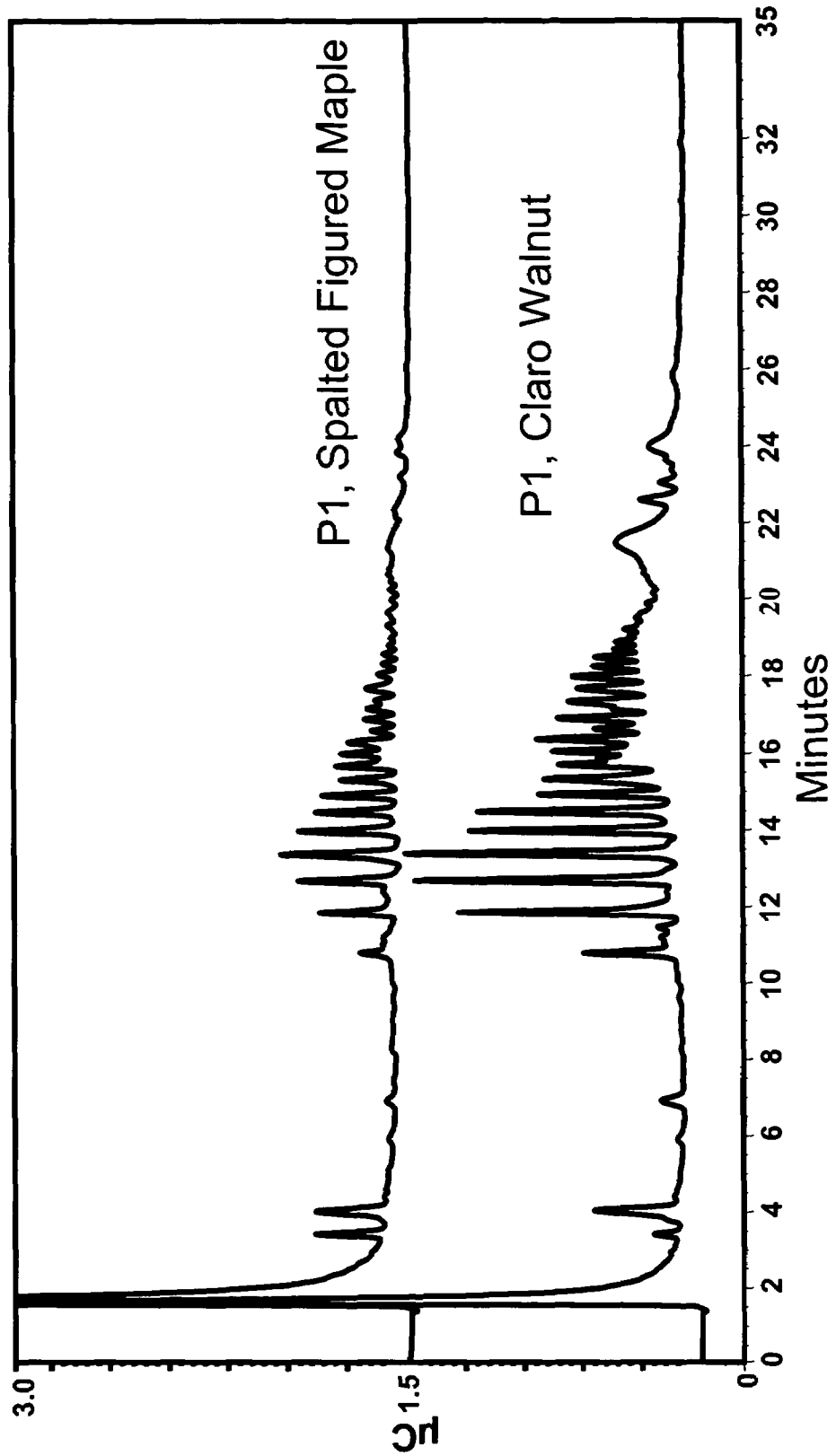
FIG. 22 shows a comparison of propanol P1 precipitates from HCl extracts of spatted figured maple versus Claro walnut.
Figure 23:
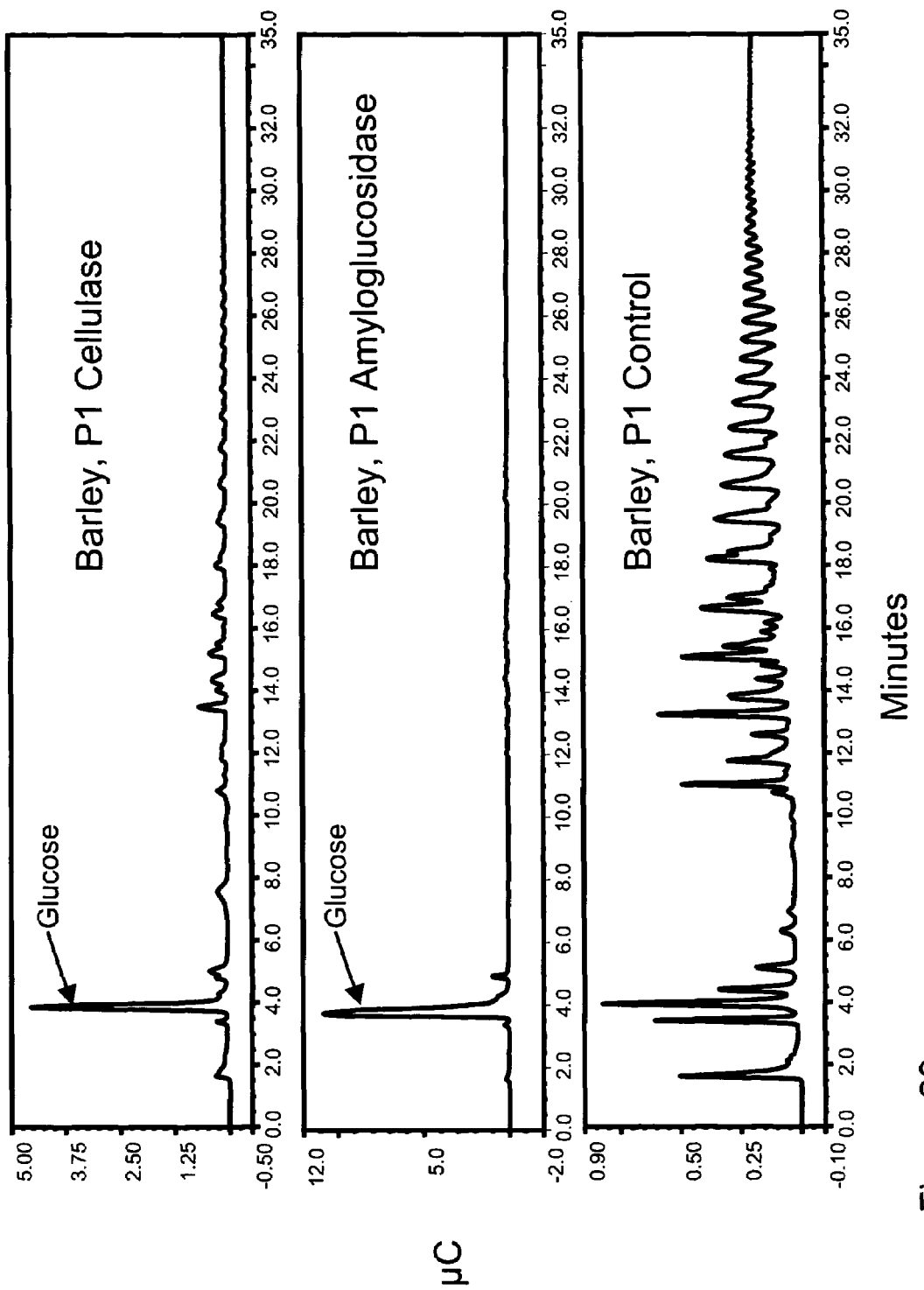
FIG. 23 shows a comparison of propanol P1 precipitates from an HCl extract of barley (grain) following incubation with a) cellulase, b) glucoamylase (amyloglucidase), and c) no enzyme (control).
Figure 24:
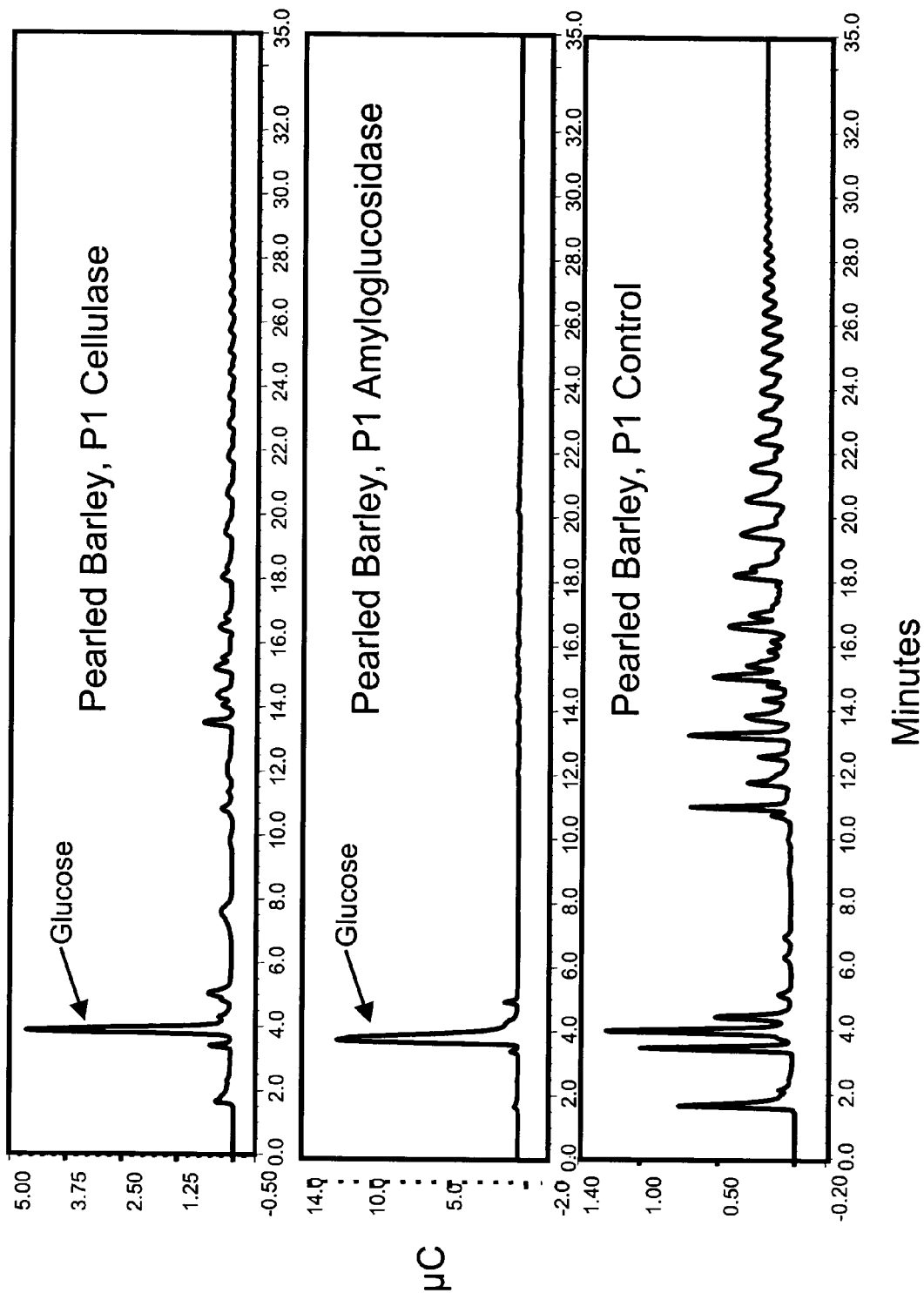
FIG. 24 shows a comparison of propanol P1 precipitates from an HCl extract of pearled barley following incubation with a) cellulase, b) glucoamylase (amyloglucosidase), and c) no enzyme (control).
Figure 25:
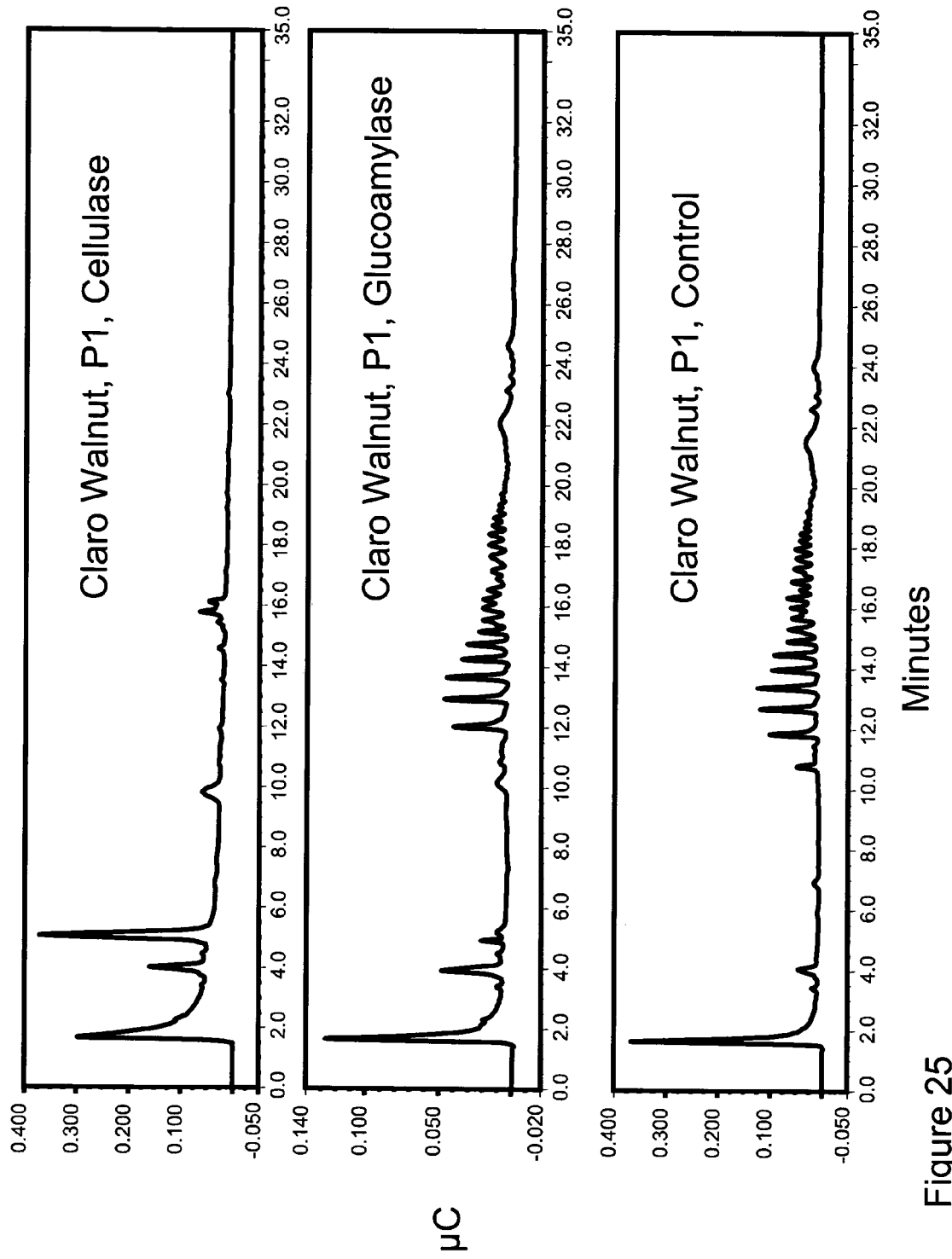
FIG. 25 shows a comparison of propanol P1 precipitates from an HCl extract of Calaro walnut following incubation with a) cellulase, b) glucoamylase (amyloglucosidase), and c) no enzyme (control).
Figure 26:
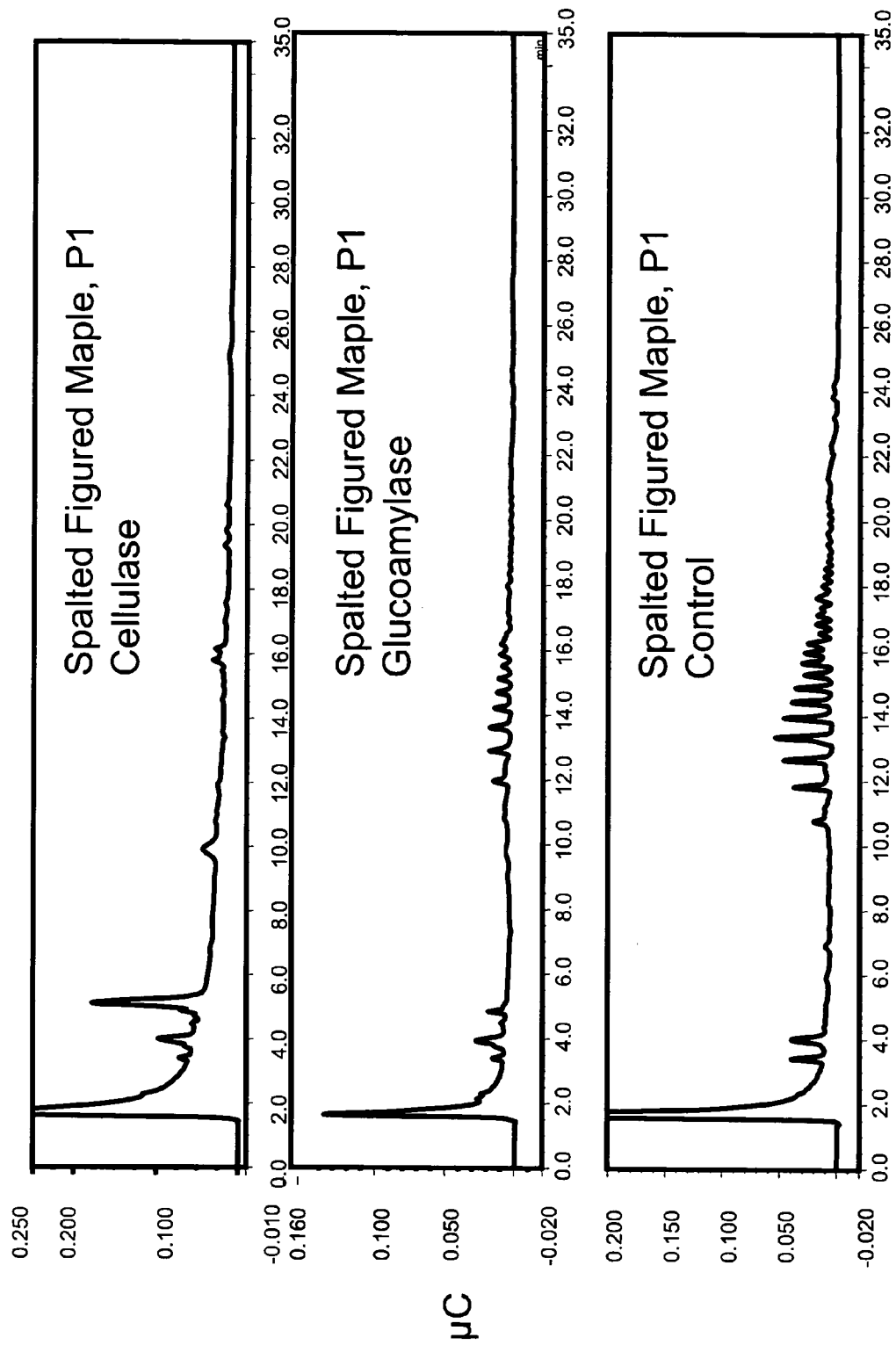
FIG. 26 shows a comparison of propanol P1 precipitates from an HCl extract of spalted figured maple following incubation with a) cellulase, b) glucoamylase (amyloglucosidase), and c) no enzyme (control)
Figure 27:
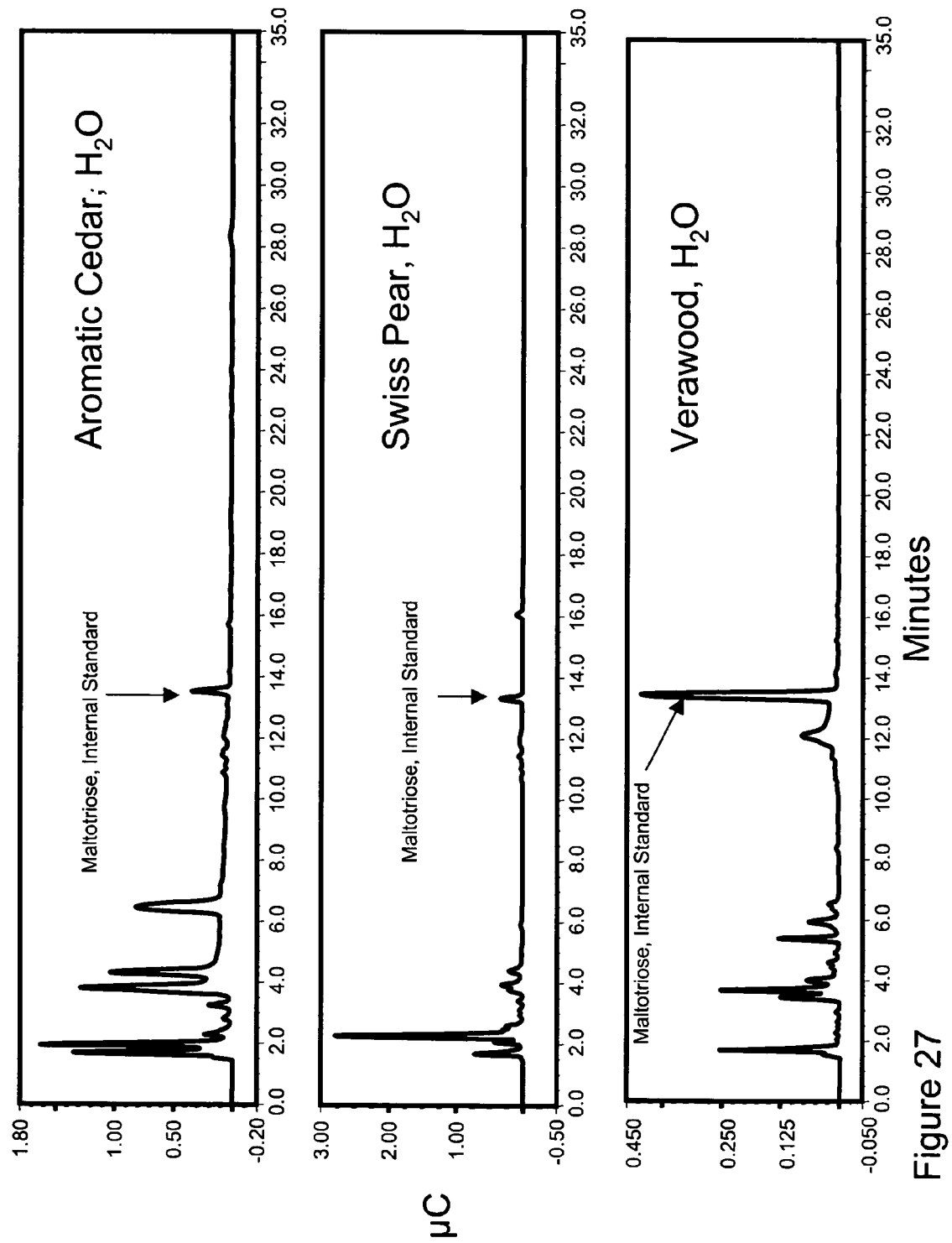
FIG. 27 shows a comparison of cold water extracts of a) aromatic cedar, b) Swiss pear (*Pyrus communis*) and c) verawood (*Bulnesia arborea*).
Figure 28:
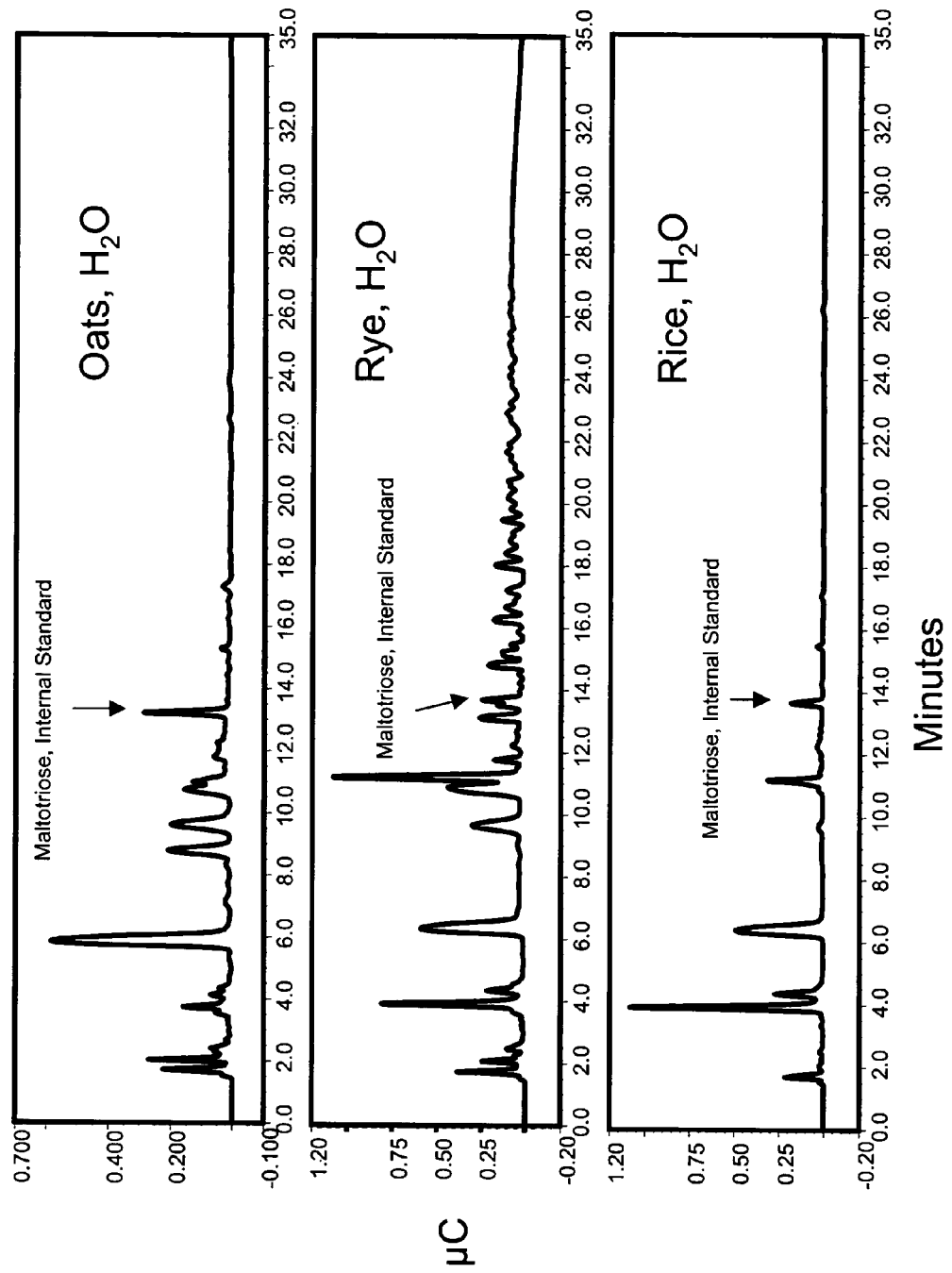
FIG. 28 shows a comparison of cold water extracts a) oats (grain), b) rye (grain) and c) rice (grain).
Figure 29:
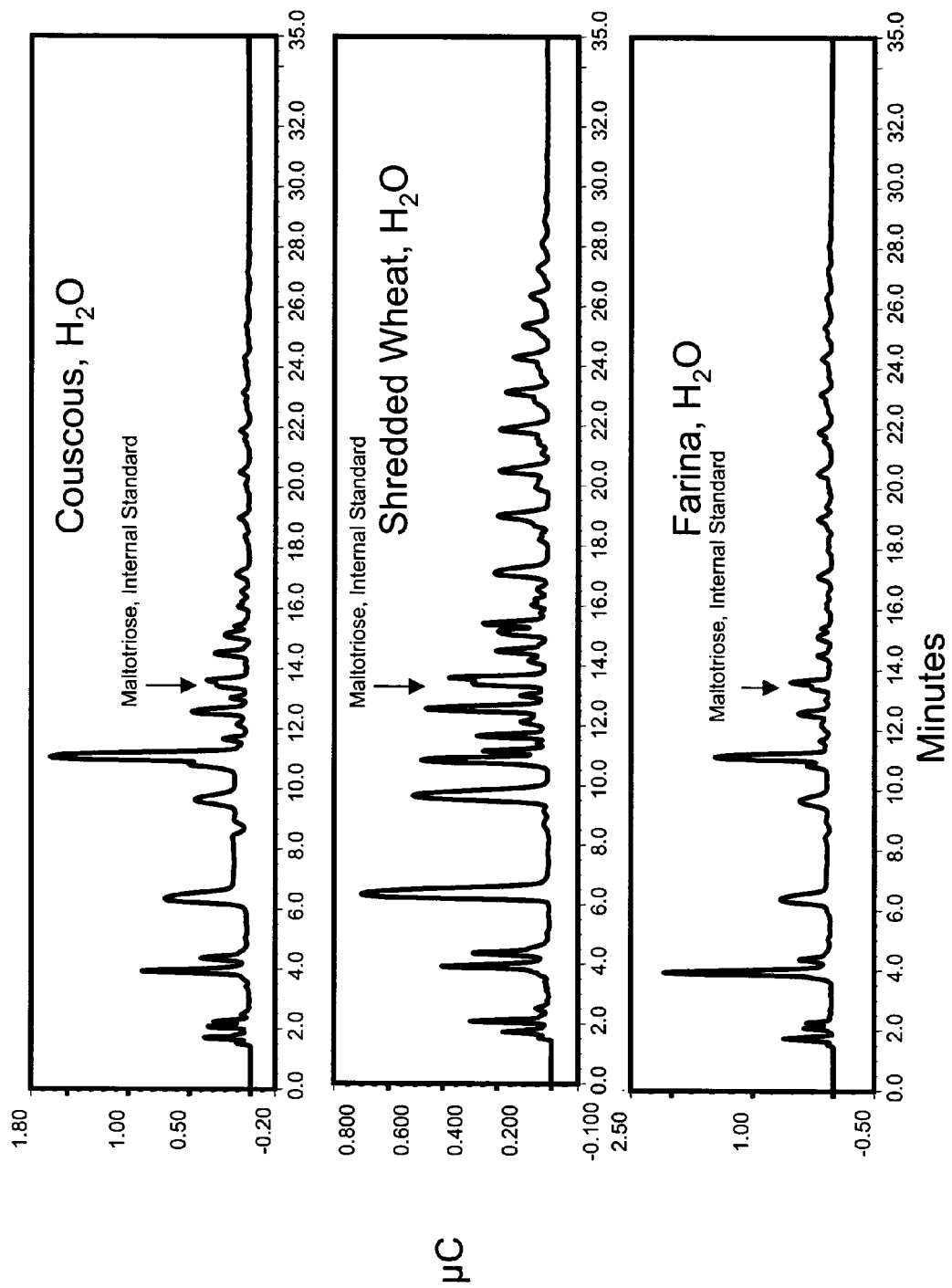
FIG. 29 shows a comparison of cold water extracts of various wheat products: a) cous cous, b) shredded wheat and c) farina.

The glycans were extracted at 100° C in 0.1N HCl which was then neutralized with an equivalent amount of 1N NaOH. If these oligomers are allowed to stand in the refrigerator at 4° C. for a few days, they precipitate out of solution. If the solution of the oligomers is desalted by passage over ion exchange resins the oligomers precipitate out immediately and will plug up a filter(0.2µ). Once precipitated from solution, the material can be resolublized by boiling in 0.1N HCl. The oligomers are reducing sugars as evidenced by the fact that they are susceptible to mild alkaline degradation, 0.1N NaOH, boiling for 5-10 min. (Whistler and BeMiller, 1958). Incubation with cellulase, in this case from *Trichoderma reesii* (Sigma) results in the degradation of the oligomers with retention times greater than 16 minutes, with a concomitant increase in oligomers with retention times of approximately 14 and 16 minutes as shown in FIG. 20. In this system cellobiose elutes at about 10.5 min.

Treatment of the oligomers with β-glucosidase, almond emulsin, results in a chromatogram with peaks quantitatively greater than the control. Presumably this is due to trimming of the longer oligomers which either are not resolved on the column or have a reduced detector response or both. The oligomers with longer retention times, greater than 20 minutes in the case of cotton fibers, can be precipitated with alcohol. Subsequently, the precipitated oligomers can be dissolved and treated with a highly purified cellulase (endoβ-1, 4-glucanase, Megazyme, Ireland) which then trims them to the peaks with shorter retention times. The only monosaccharide released by this cellulase treatment is glucose. A preliminary investigation of the monosaccharide composition of the oligomers extracted from 21 DPA fibers has shown that the most prevalent monosaccharide is glucose, but that these oligomers also contain galactose, mannose, m-inositol and glycerol.

Figure 2:
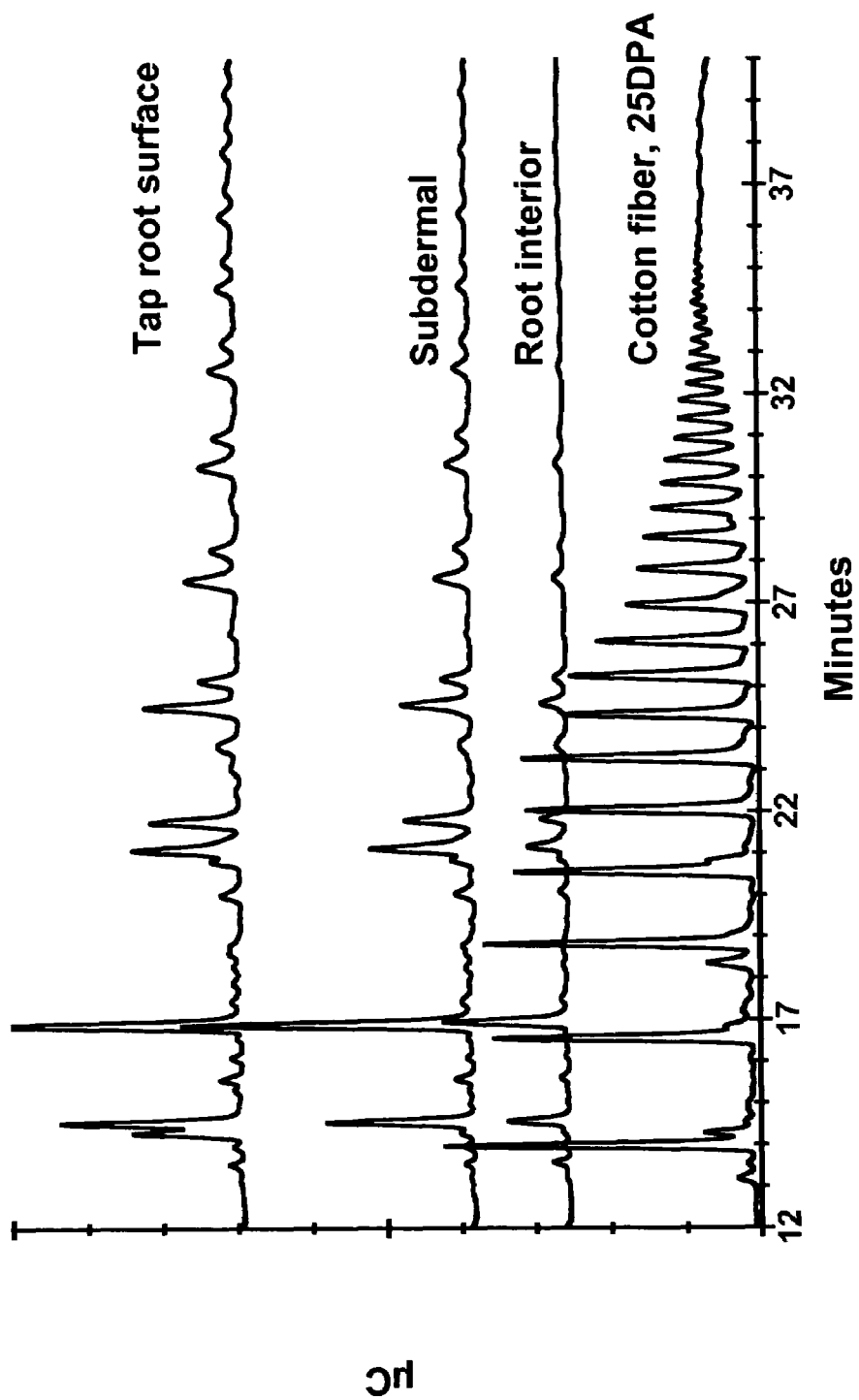
FIG. 2 compares multimers extracted from a normal cotton fiber with multimers extracted from portions of sugar beet root to demonstrate that some of these carbohydrates are found in cell walls of widely divergent plants; here the multimers from each zone are the same but their abundance is increased in tissues with a higher degree of organization.

Perhaps the most exciting and unexpected discovery was the finding that following the aqueous extraction it is possible to extract a multimer fraction by boiling for 30 minutes in dilute 0.1M HCl. Presumably these multimers represent some component that connects the paracrystalline cellulose within the wall. The multimers are reducing sugars, as are the GC-2 (glycoconjugate) group of compounds disclosed in earlier patent applications, indicating a non-typical glycan linkage in the polymers. Hydrolysis (acid) of individual peaks has demonstrated that they contain galactose, glucose and mannose. In classical plant cell wall research dilute mineral acids are sometimes used to extract pectins or "pectic materials" which, by definition, contain galacturonic acid residues. Clearly, the multimers are neither pectins nor pectic materials. Further, it is necessary to first perform the cold aqueous extraction so that the multimers are not obscured by the GC-1 and GC-2 compounds. Further analysis of the multimers of normal fibers has revealed that the major difference between successive multimers is an addition of glucose units. That is, successive multimers in a series have comparable amounts of galactose and mannose but different amounts of glucose. It appears certain that many of these same multimers are found in a variety of cell walls. FIG. 2 shows that HCl extracts of sugar beet root tissue contains a multimer series wherein several of the compounds exactly overlap some of the cotton multimers.

Universality of the Method

The same method of extraction with hot weak acid can be applied to virtually any plant material. The pattern of oligomers released is unique for each plant and tissue and further demonstrates effects of developmental state and growth conditions. Differences in growth conditions may reflect the influence of environmental pollutants. This method of analysis can be applied to any plant material including foodstuffs. The method has been applied to food grains such as wheat, corn, rye, rice and oats. Each type of grain shows a unique profile of soluble mono- and oligosaccharides, a unique profile of oliogmers released by the hot weak acid, as well as unique profiles of the redissolved alcohol precipitates and in some cases the enzymatic digest of the redissolved alcohol precipitates.

The oligomers which are degraded to glucose by glucoamylase are, by definition, constituents of starch. However there are fractions which are not completely degrade by the glucoamylase. Barley contains a mixed β-1,3, β-1,4 glucan which is a major constitiuent of dietary fiber. Therefore the glucose liberated by the endo β-1,4-glucanase from barley P1 probably originates from the barley glucan while the glucose liberated by the amyloglucosidase from the barley P1 probably originates from the amylose or starch, an α-1,4-glucan. There is a very small amount of cross activity against starch by the cellulase and against β-glucan by the amyloglucosidase but such activity is less than 0.001% of the total activity of the enzyme.

Figure 3:
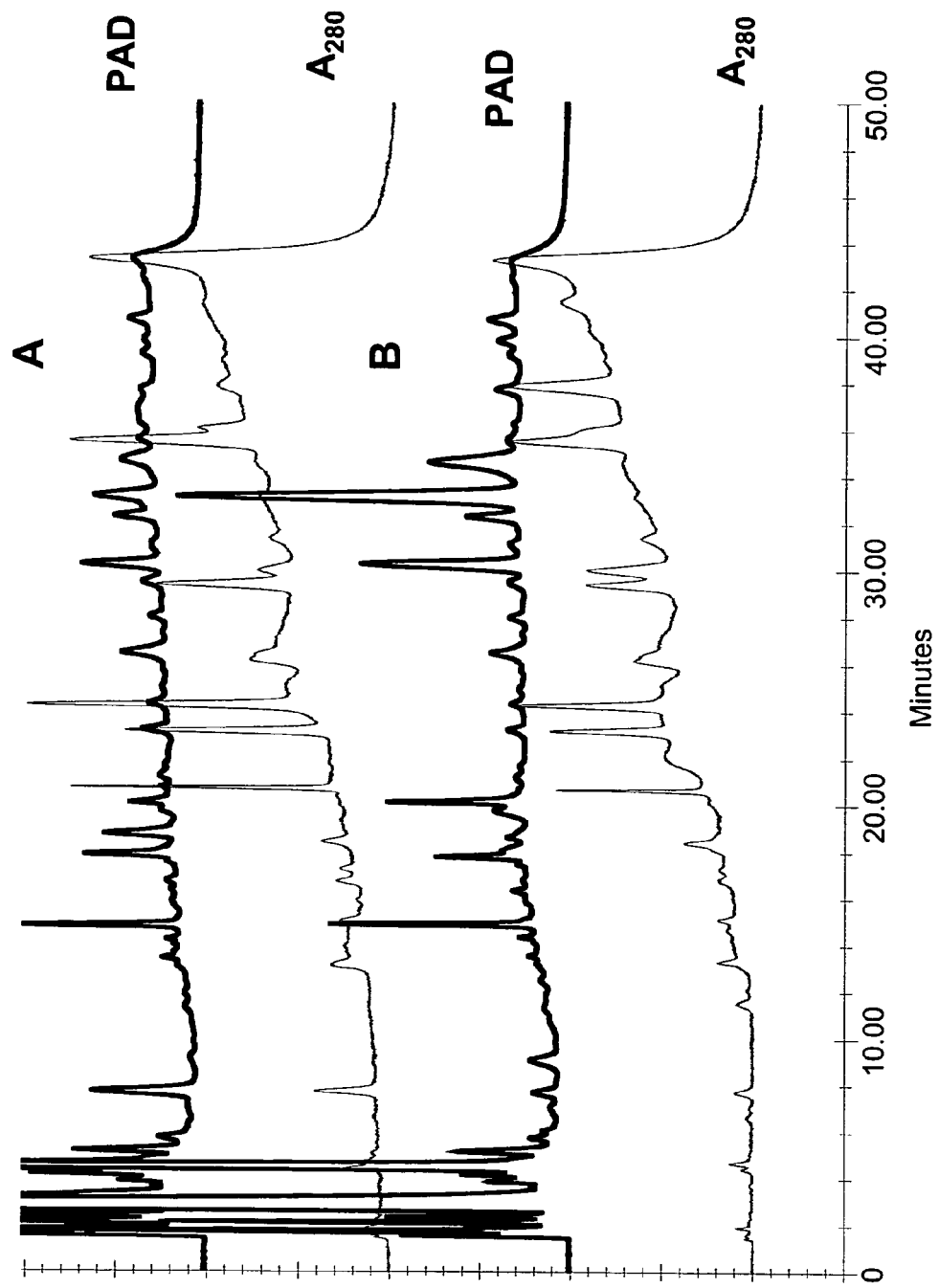
FIG. 3 shows multimers extracted from a) a marine alga (*Macrocystis* sp.) compared with those extracted from b) a marine flowering plant (*Zostera* sp.).

It would appear that the multimers revealed by the method of the present invention are indeed a "universal" feature of plant cell walls. A prime example can be seen in FIG. 3 which compares a brown alga seaweed (a kelp) *Macrocystis* with a marine flowering plant eelgrass—*Zostera*. Despite the great evolutionary distances that separate these organisms they display marked similarities in cell wall content as revealed by the current method of analysis.

The inventive multimer (oligomer) extraction is ideally suited for evaluating cotton fiber samples for a number of defects that plague the textile industry. Motes are immature, short fibers that lower the quality of cotton. Although their presence can be assessed by microscopic inspection of fibers, they also give a unique carbohydrate pattern allowing determination of mote contamination from bulk samples. The method has also been utilized in the analysis of glycogen from oysters, bovine liver, rabbit liver and human liver. Glycogen is a storage polysaccharide synthesized on a core protein, glycogenin. The polysaccharide portion is an α-1,4-glucan with an α-1,6 branch point approximately every six residues. The method is applicable to both storage glucans, starch and glycogen, which are α-linked glucans with highly branched structures as well as to sources of cellulose which is a linear β-1,4-linked glucan.

Characterization of Oligomers.

The major difference between successive oligomers from normal cotton fibers is in the relative glucose content. That is, successive oligomers in a series have comparable amounts of galactose and mannose but different amounts of glucose. It is not yet known whether the apparently suppressed production of oligomers in the drought stressed plants follows this pattern. However, many of these same oligomers are found in a variety of cell walls although the data is not presented here.

Alcohol Precipitation

Figure 17:
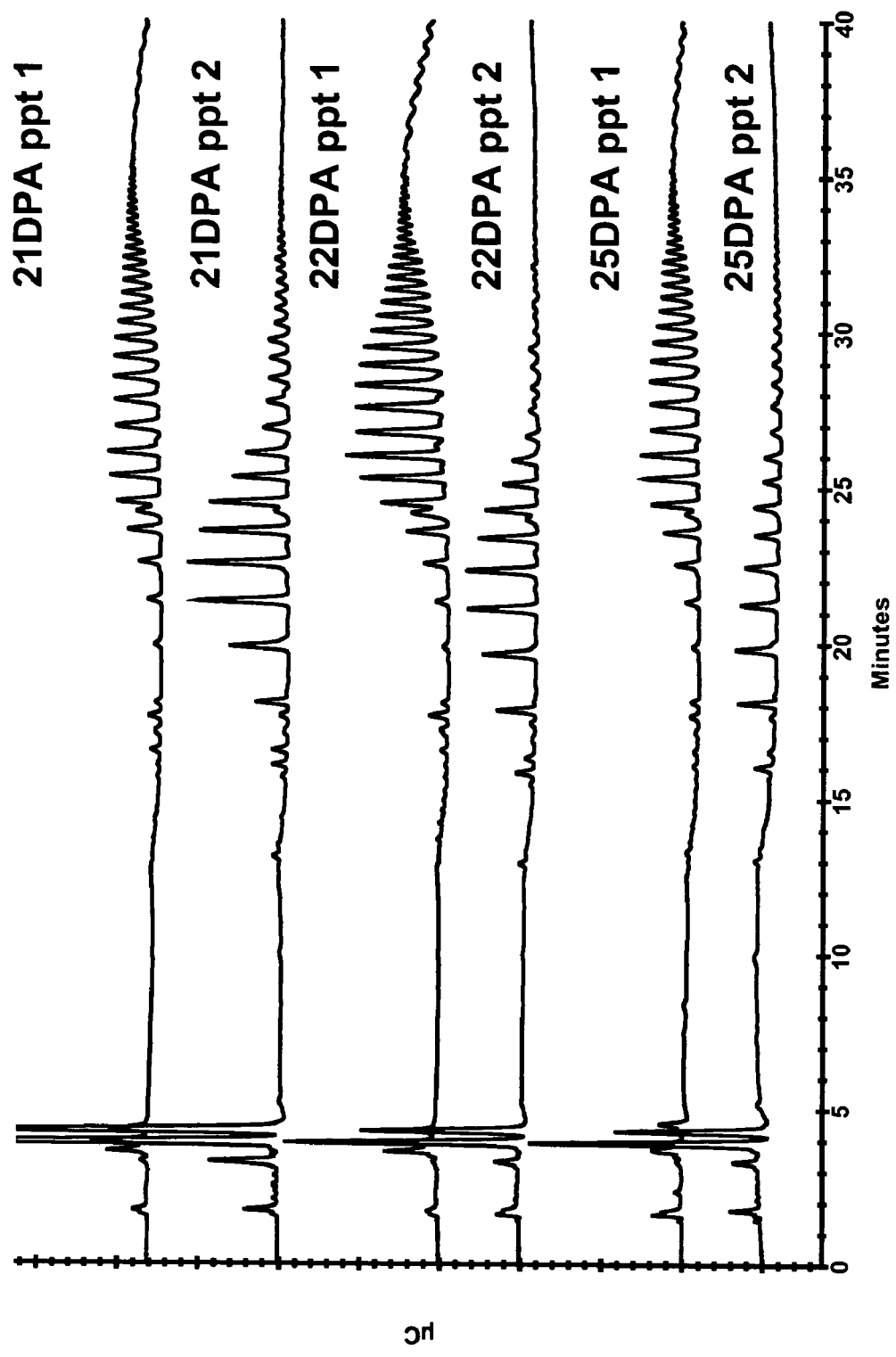
FIG. 17 shows the ethanol precipitates of HCl extracts from cotton fibers from bolls collected at 21, 22 and 25 days postanthesis (DPA).
Figure 18:
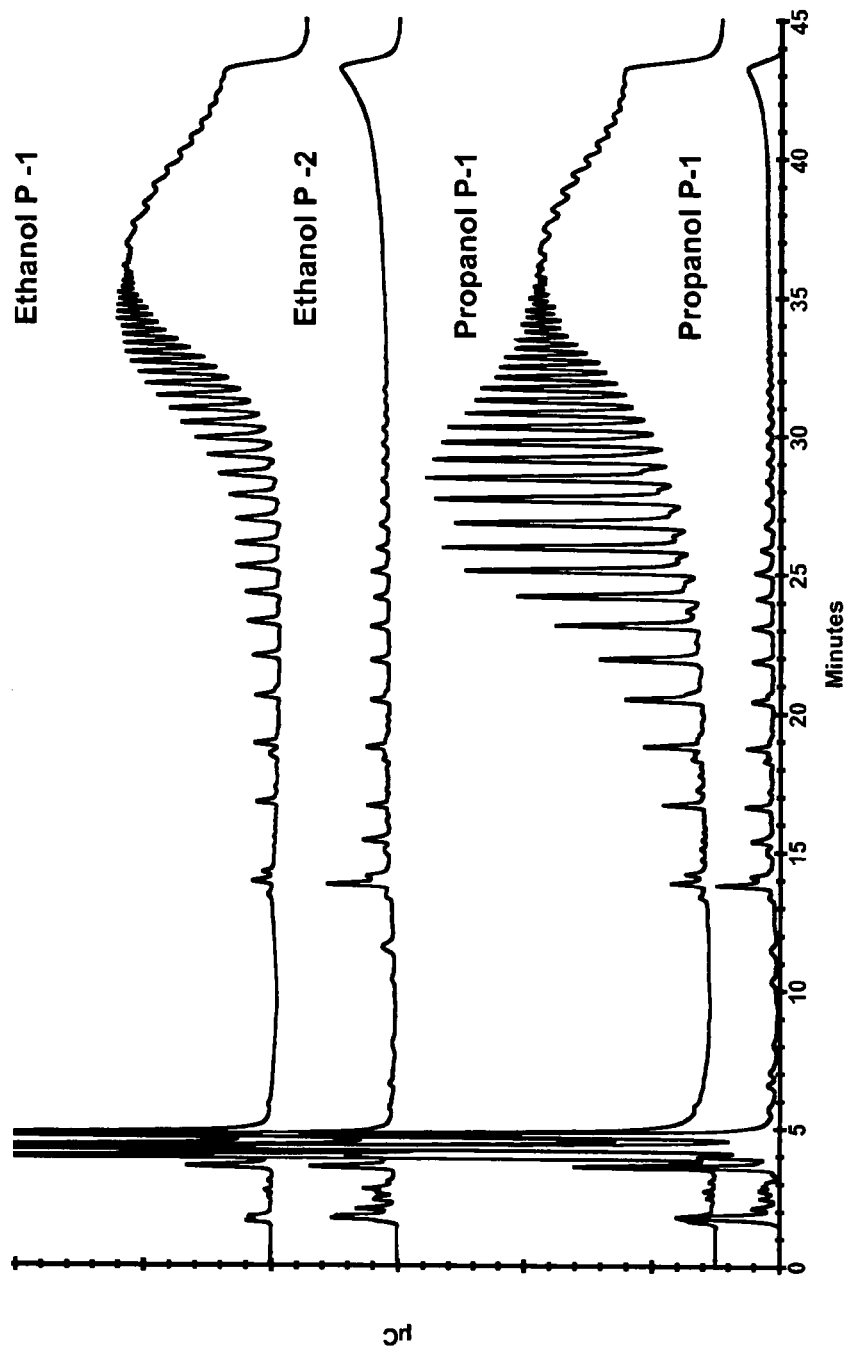
FIG. 18 shows the ethanol and propanol precipitates of HCl extracts from cotton fibers from bolls collected at 21 DPA.
Figure 19:
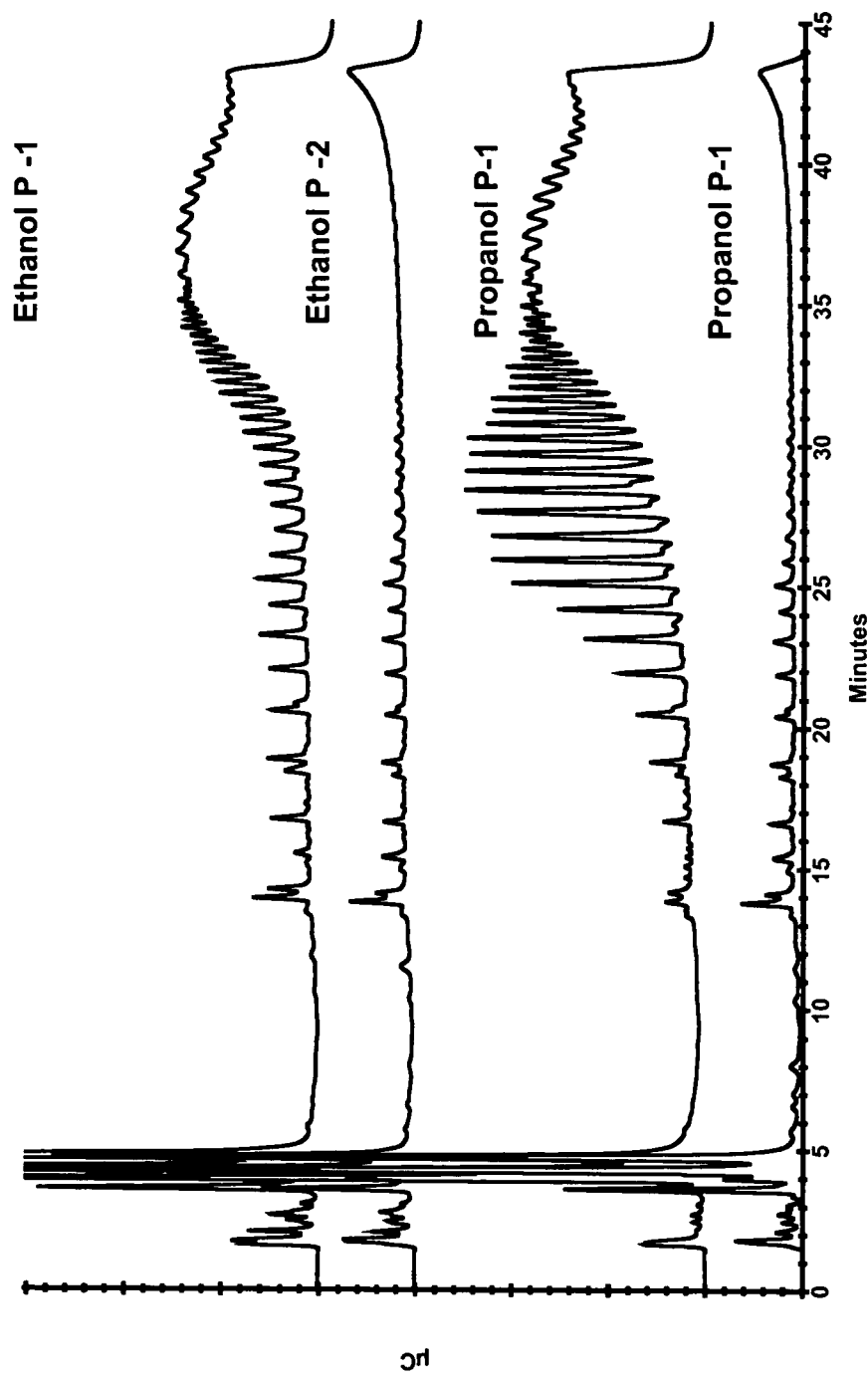
FIG. 19 shows the ethanol and propanol precipitates of HCl extracts from cotton fibers from bolls collected at 22 DPA.

The ethanol precipitates of the HCl extracts of fibers from bolls collected at 21, 22 and 25 DPA are shown in FIG. 17. A comparison of the ethanol and propanol precipitates of fibers from bolls collected at 21 and 22 DPA are shown in FIGS. 18 and 19. Propanol precipitates were subjected to cellulase for incubation times up to 90 min which shows a shift toward earlier eluting peaks as shown in FIG. 20. In all cases a great amount of glucose was released. The monosaccharide peaks are not shown in their full magnitude so that the oligosaccharide peaks can be shown.

Source Identification of Woods and other Plant Materials

The above-described experiments indicated that plant cell wall materials such as cotton give surprisingly consistent patterns of extracted multimers. This suggested that the method might yield unique "fingerprints" that could be used for identifying the origin of cellulosic materials for forensic and other purposes (e.g., quality control of wood pulps, etc.). The present method of analysis has now been extended to a wide variety of cellulose containing materials (many of them exotic woods). My current working hypothesis is that cellulose is synthesized on a glycosylated protein template and the oligomers (multimers) released by the treatment with dilute HCl by boiling for 30 min are derived from this glycosylated protein template. Therefore, it is logical to assume that such oligomers will be released from virtually all cellulose containing materials which are derived from a plant cell wall, assuming that virtually all plant materials will contain templated polysaccharides that have not yet been tightly incorporated into the cell wall. Each species of plant would be expected to have slightly different enzymes and pool sizes of various cell wall precursors. This would lead to each type (species) of wood—essentially composed of secondary cell walls containing cellulose and lignin—having unique cellulose characteristics. In addition, analagous oligomers are found in plant tissues which are not characterized by secondary cell walls. They have been extracted from food grains such as wheat, oats, rye, barley and rice. It is quite possible and likely that these oligomers comprise that fraction of the food grains which is referred to as "soluble fiber" by the dietary field since they are likely not digested in the human gastrointestinal system.

Figure 12:
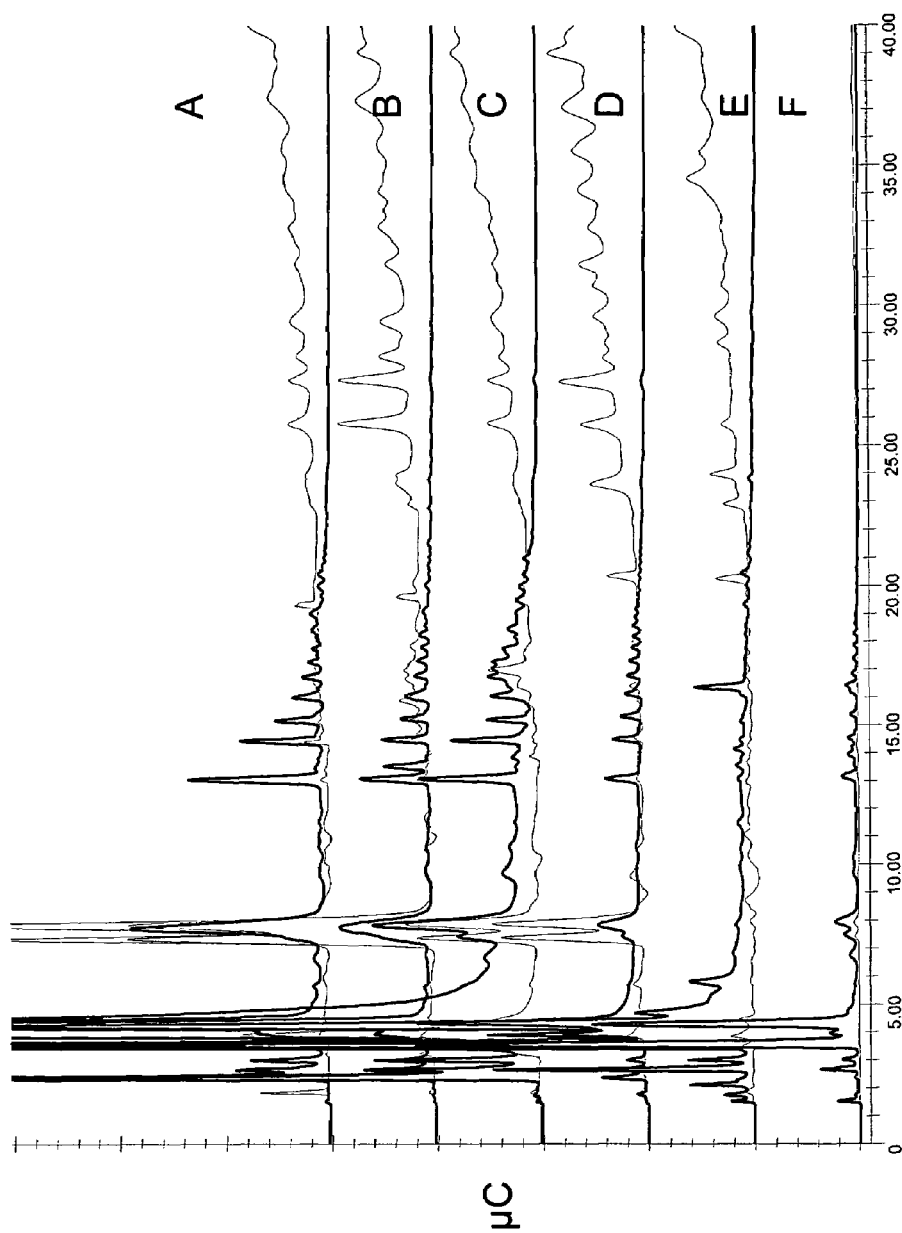
FIG. 12 shows the variations in multimer patterns extracted from different woods (in each instance the light trace represents the UV absorbance): a) spatted maple (*Acer* sp.); b) European beech (*Fagus* sp.); c) pau ferro; d) koa (*Acacia* sp.); e) aromatic cedar; f) cherry (*Prunus* sp.).
Figure 13:
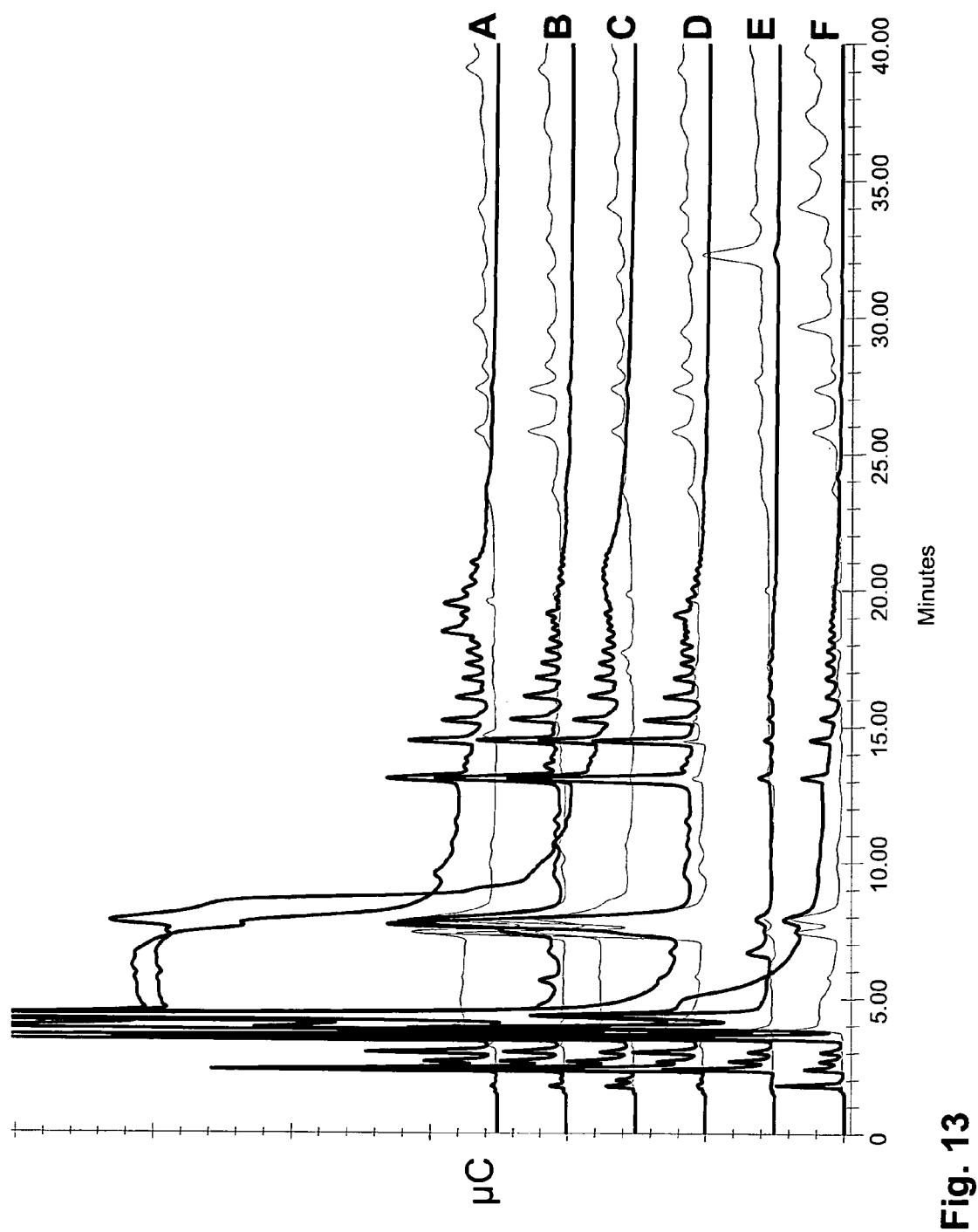
FIG. 13 shows the variations in multimer patterns extracted from different woods (in each instance the light trace represents the UV absorbance): a) English walnut (*Juglans* sp.); b) English yew (*Taxus* sp.); c) English chestnut (*Castanea* sp.); d) English brown oak (*Quercus* sp.); e) Honduras rosewood; and f) Madagascar rosewood.
Figure 14:
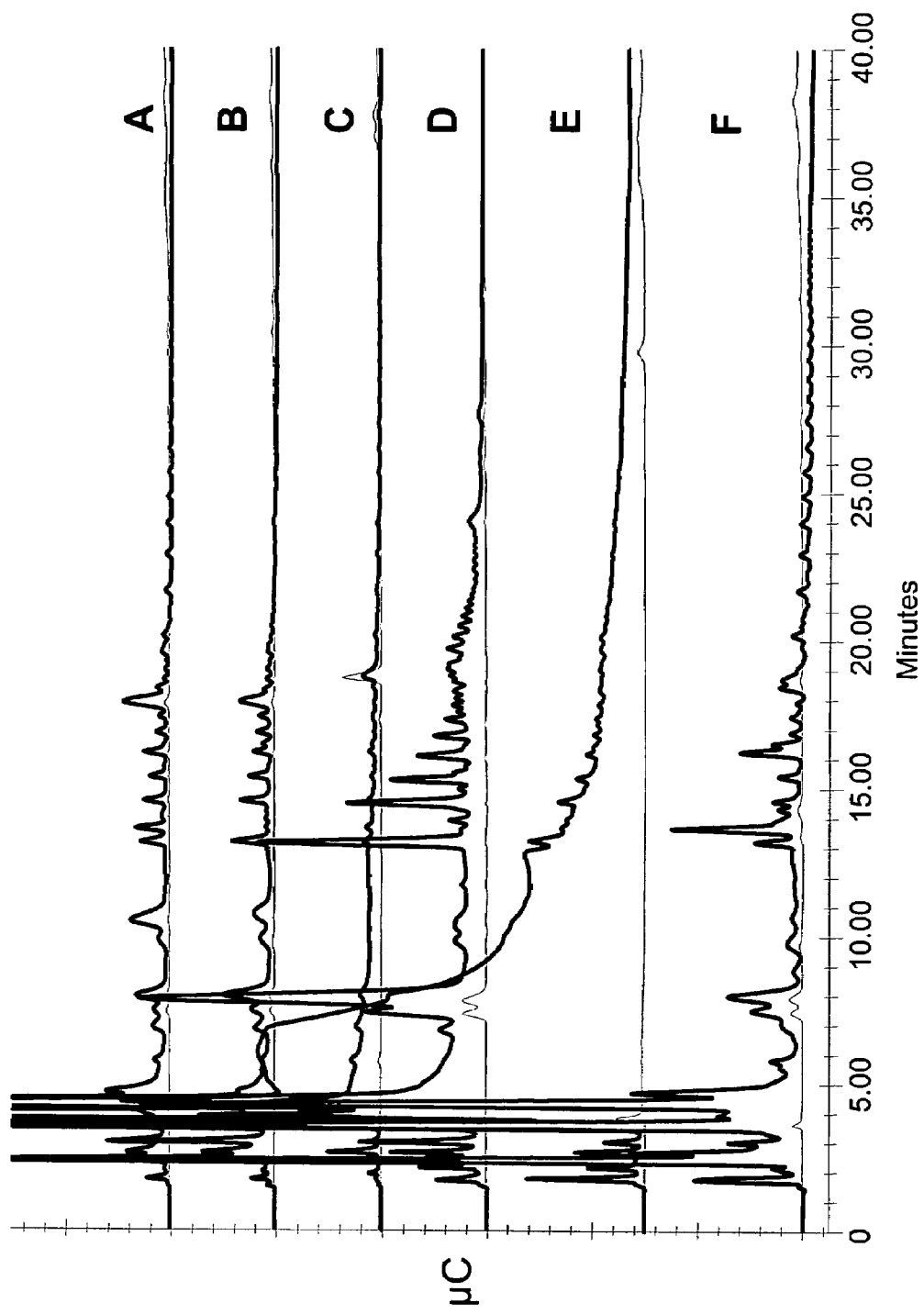
FIG. 14 shows the variations in multimer patterns extracted from different woods (in each instance the light trace represents the UV absorbance): a) basswood (*Tilia* sp.); ash (*Fraxinus* sp.); c) blood wood; d) English brown; e) mesquite (*Proscopis* sp.) and f) Swiss pear (*Pyrus* sp.).
Figure 15:
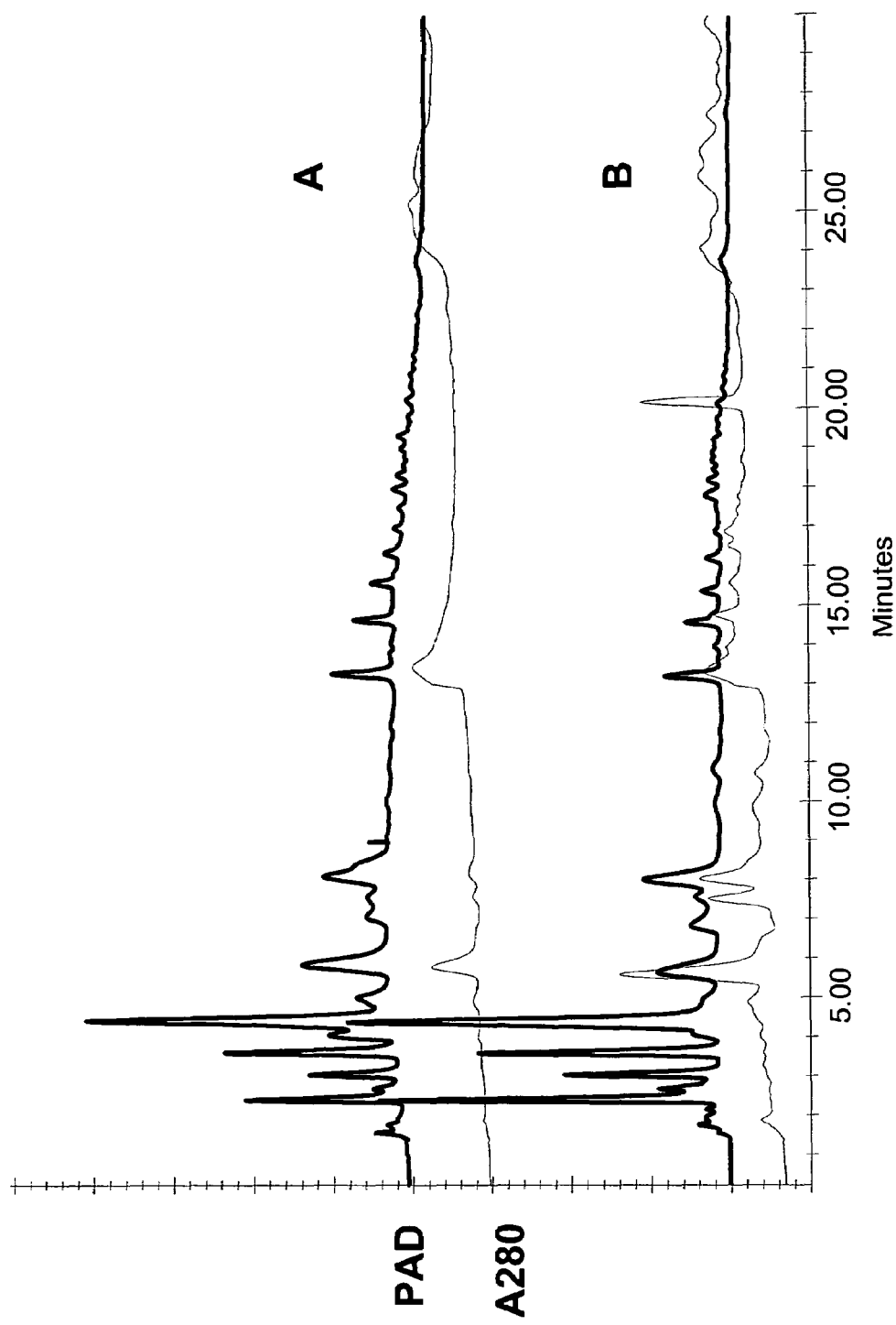
FIG. 15 shows the variations in multimer patterns extracted from old and new teak (in each instance the light trace represents the UV absorbance): a) old teak removed from a boat deck after 19 years service—scale expanded 10×; b) new teak—scale not expanded.
Figure 16:
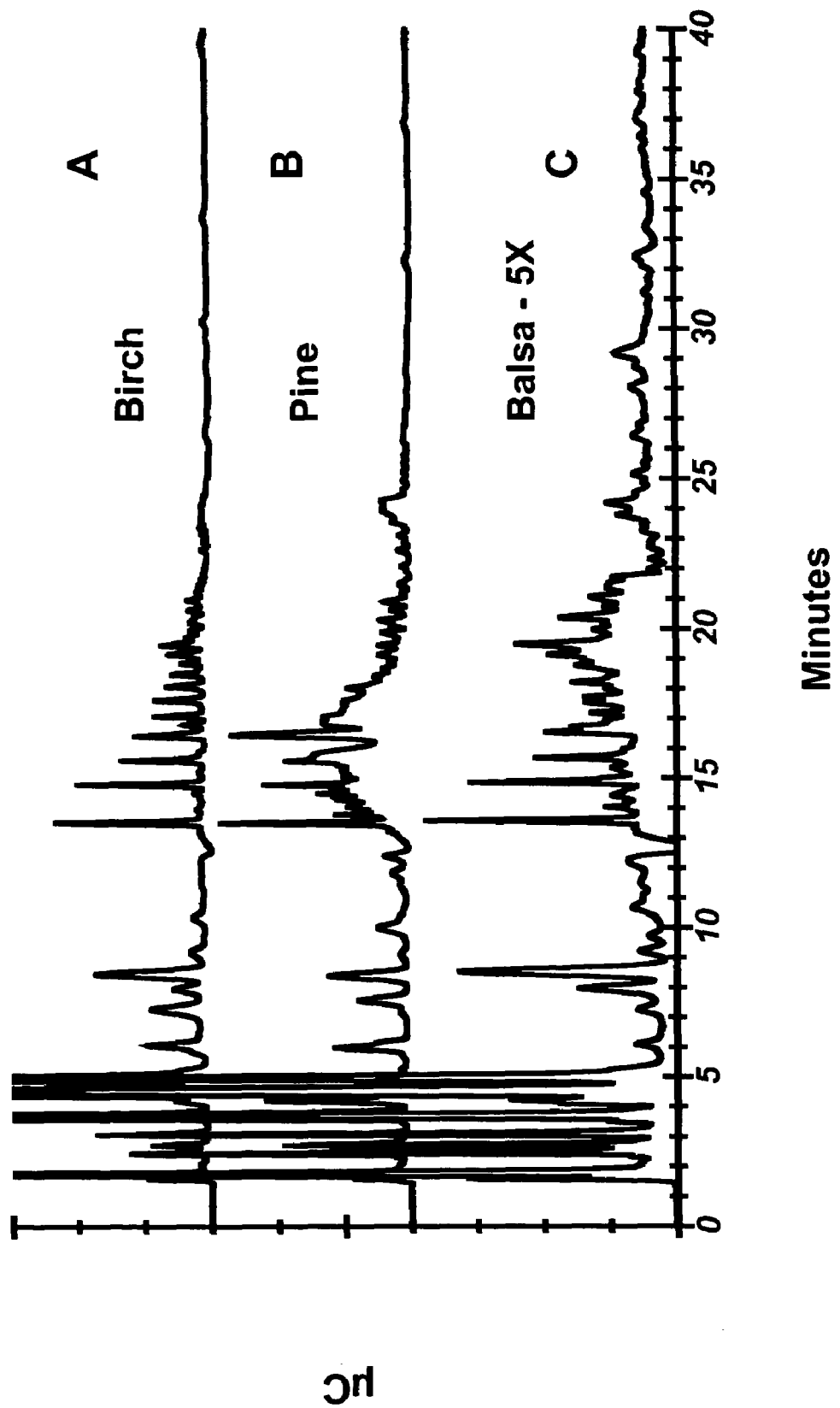
FIG. 16 shows the variation in multimer patterns extracted from (a) birch, (b) pine and (c) balsa (the balsa scale is expanded 5×).

A survey of several kinds of wood has been performed with the method of the present invention The results of this survey are show in FIGS. 12-14. To date the following kinds of wood have been analyzed: birch, pine, balsa, basswood, ash, English brown oak, mesquite, Swiss pear, English walnut, English yew, English chestnut, English brown oak burl, Honduras rosewood, Honduras mahogany, Madagascar rosewood, spatted figured maple, European beech, pau ferro, koa, aromatic cedar, cherry as well as both new teak and old weathered teak (FIG. 15). In all cases each species of wood has a unique "signature" or "fingerprint". Some are very similar such as pau ferro (*Mahaerium scleroxylon*) and ironwood, but when the chromatograms are closely compared one can distinguish unique species specific differences. Difference in the "fingerprints" can be readily seen in FIG. 16 which shows extracts from less exotic woods, namely birch, pine and balsa. Birch and pine vary particularly in the peaks between 15 and 20 minutes retention. Balsa has a lower level of multimers and is presented on a five-fold expanded scale. The measurement of UV absorbance at 280 nm adds an additional dimension. This absorbance reflects the presence of phenolic compounds and could represent phenolic amino acids in proteins, but it also can be the result of other phenolic compounds such as the constituents of lignin in wood. In the case of teakwood (FIG. 15) new wood was compared with old teak, which had been removed from the deck of a boat after being exposed to weather and the elements for 19 years. The UV absorbing compounds are almost completely gone from the old teak while the new teak has them in abundance. The chromatogram of the dilute acid extracted oligomers of the old teak is essentially identical to that of the new teak when the scale is amplified 20× for purposes of comparison. This is probably the result of much of the oligomeric material being extracted by repeated exposure to both salt and fresh water as well as exposure to sunlight.

Figure 4:
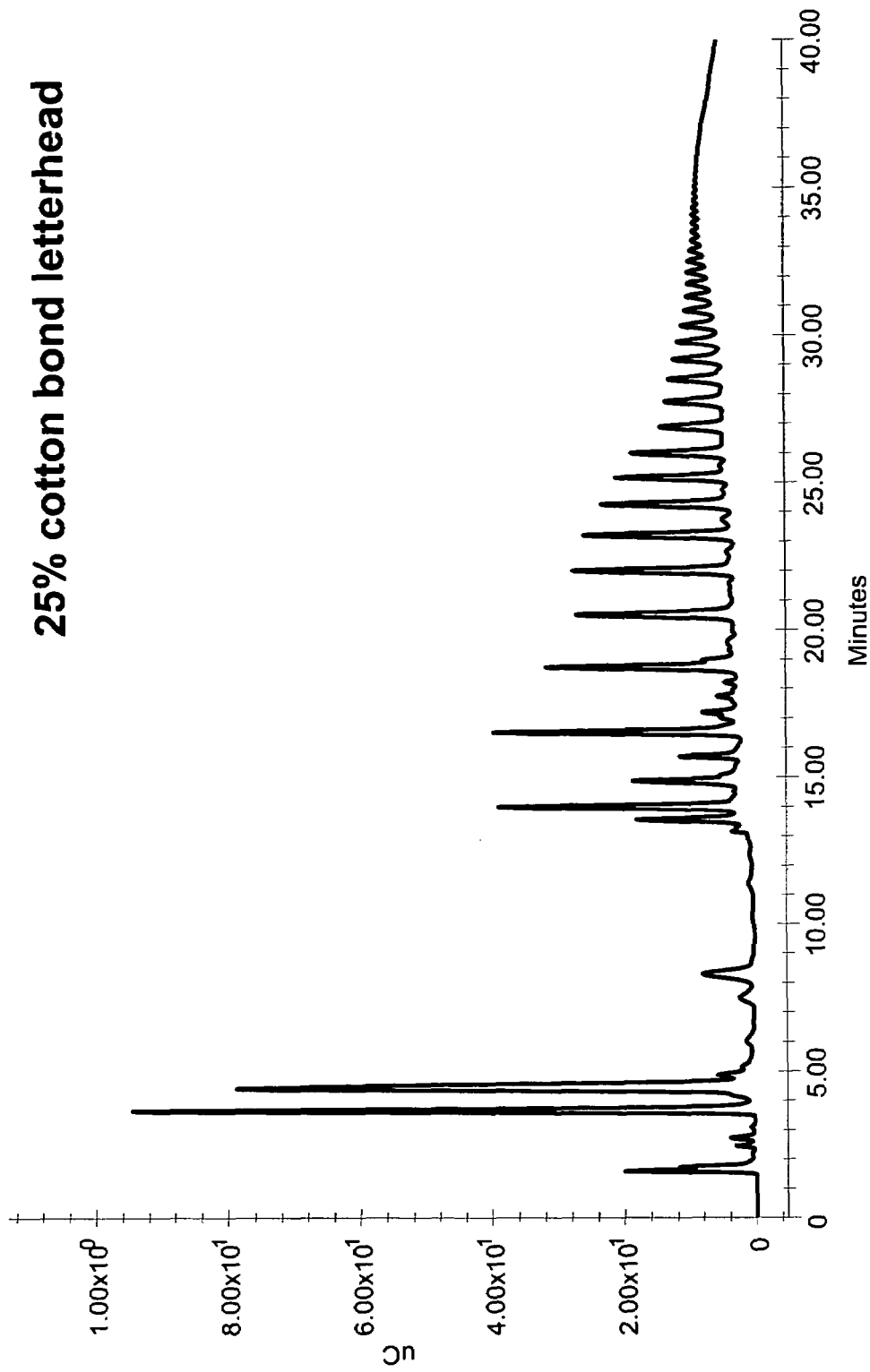
FIG. 4 shows multimers extracted from 25% cotton bond paper.
Figure 5:
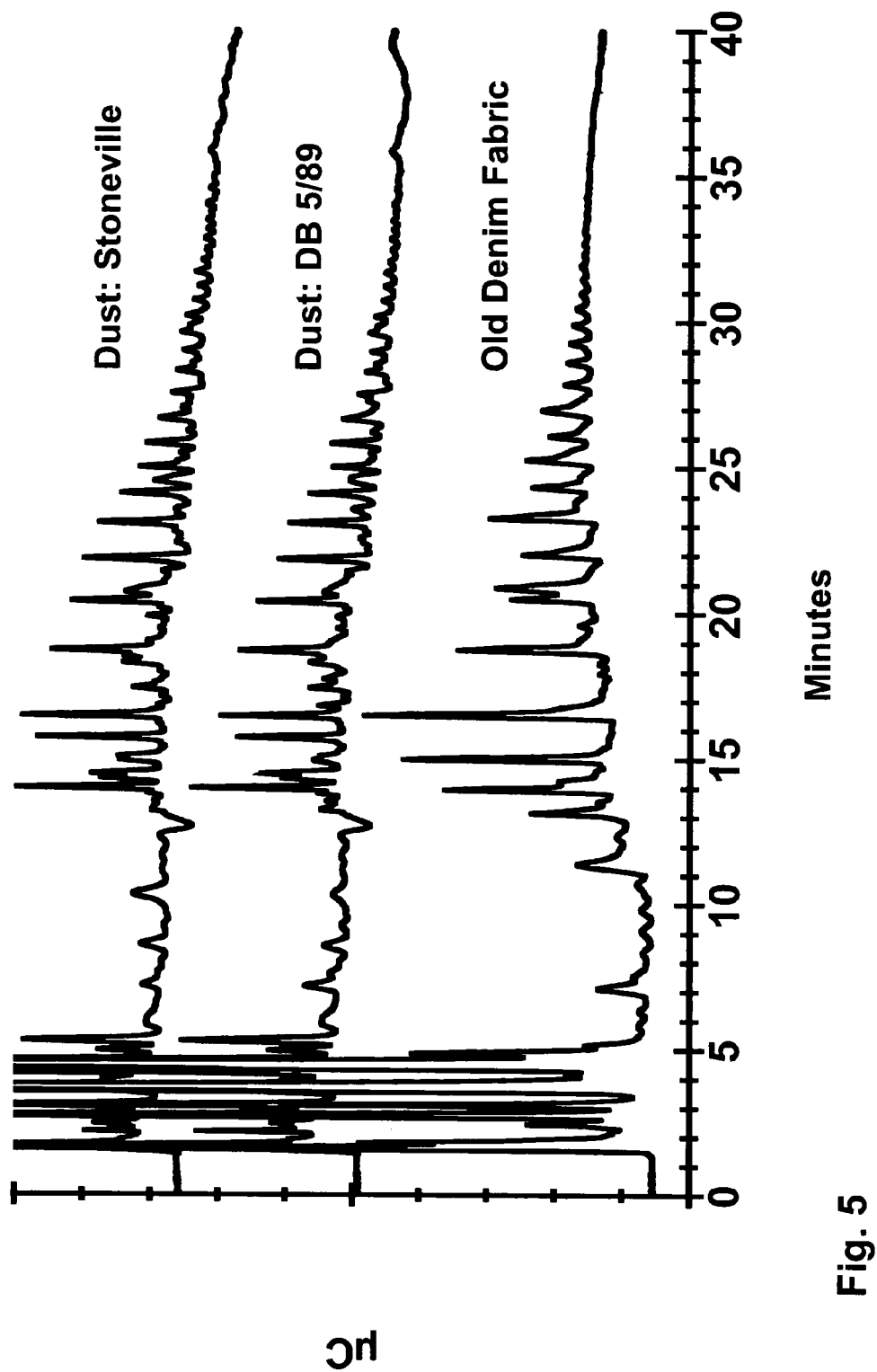
FIG. 5 shows the multimers extracted from cotton dust and from old (heavily laundered) denim fabric.
Figure 6:
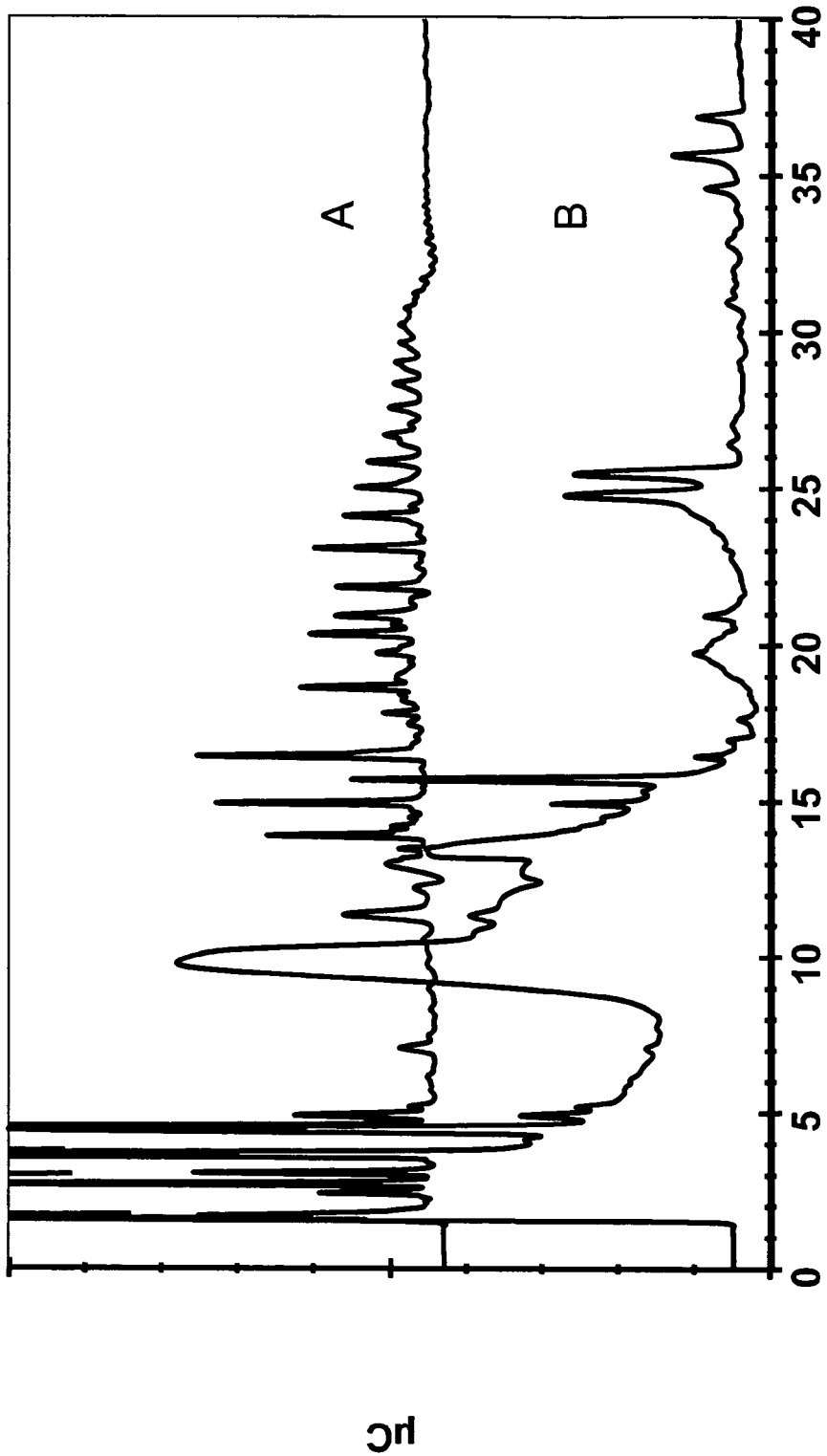
FIG. 6 shows multimers extracted from old (heavily laundered) denim jeans (a) as opposed to permanent press pants (b) in which the multimers appear to have been cross-linked.
Figure 7:
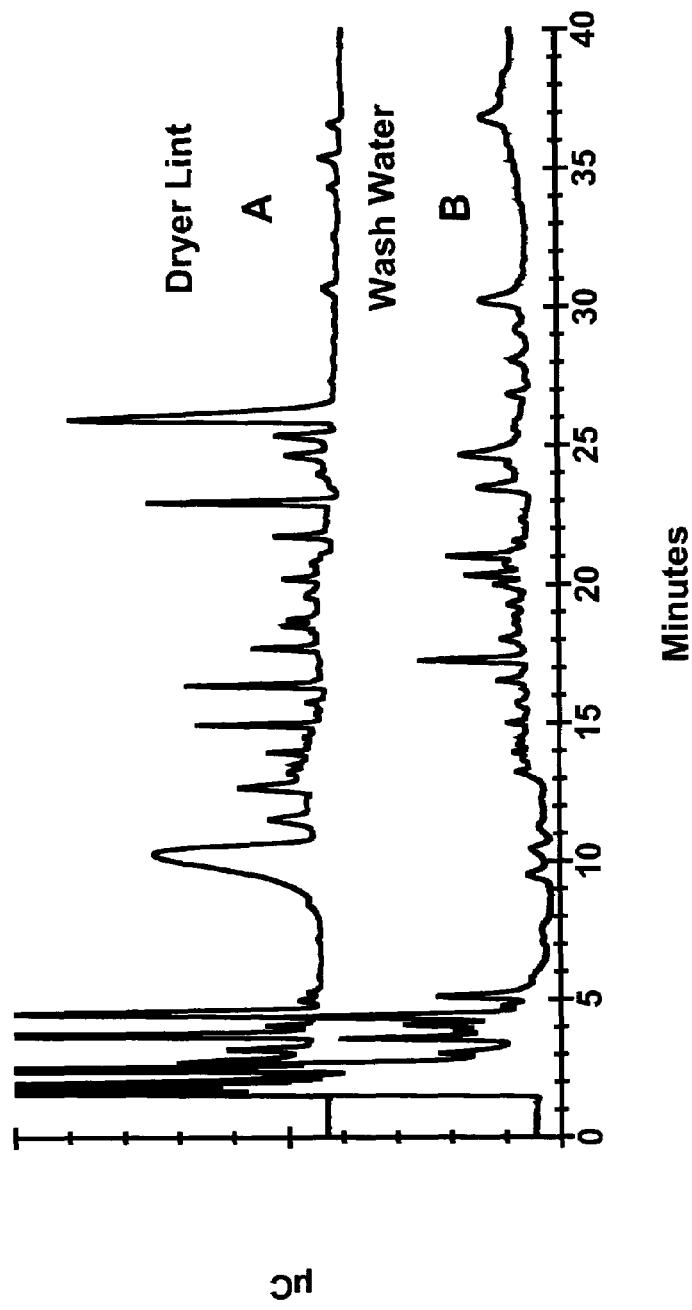
FIG. 7 shows multimers extracted from dryer lint (a) (similar to whole fabric) versus multimers found in wash water (b) released from cotton fabric by laundering.
Figure 8:
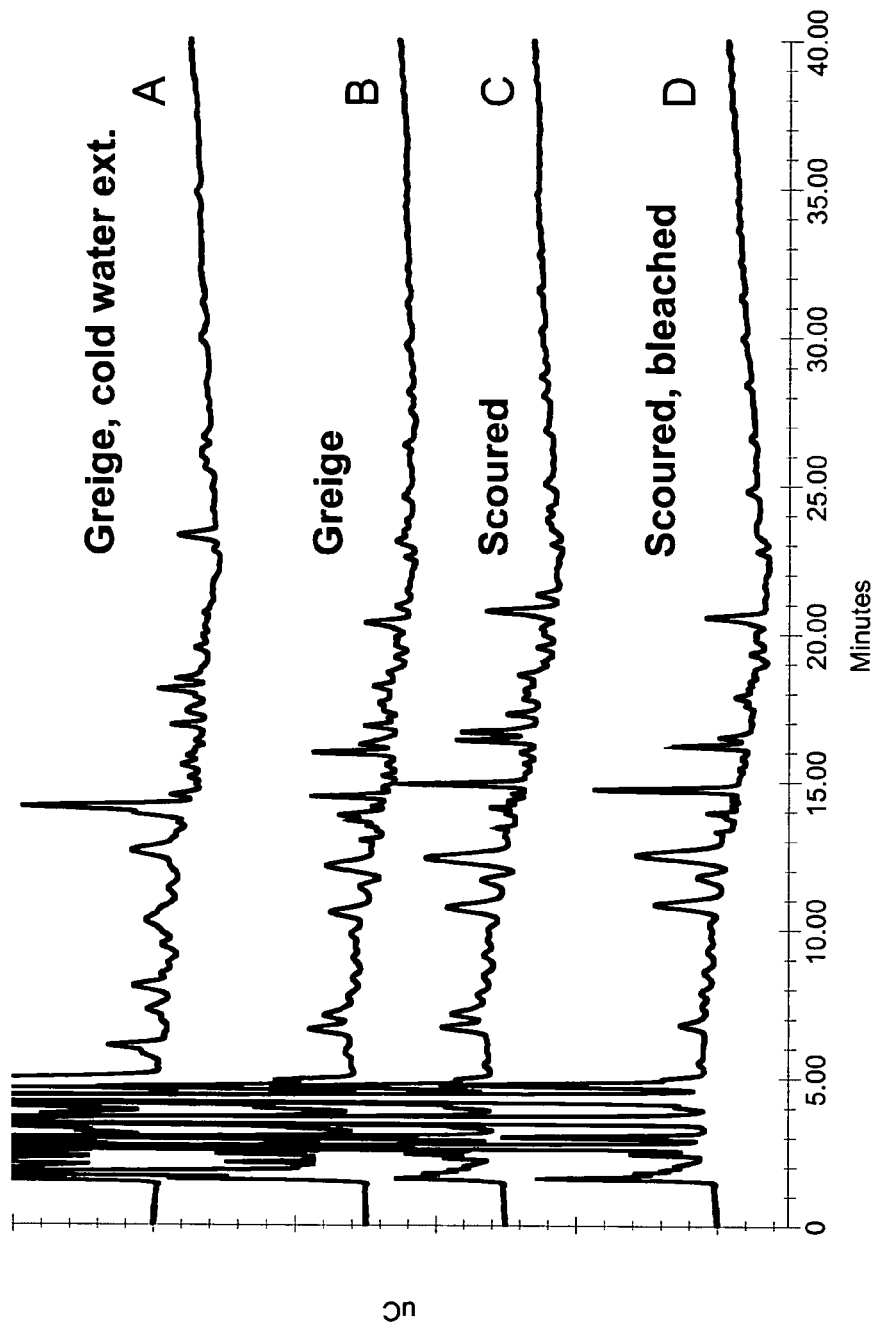
FIG. 8 shows multimers extracted from cotton fabrics at various stages of processing: a) Greige stage with cold water extraction; b) Greige stage; c) scoured fabric; and d) scoured fabric that has been bleached.
Figure 9:
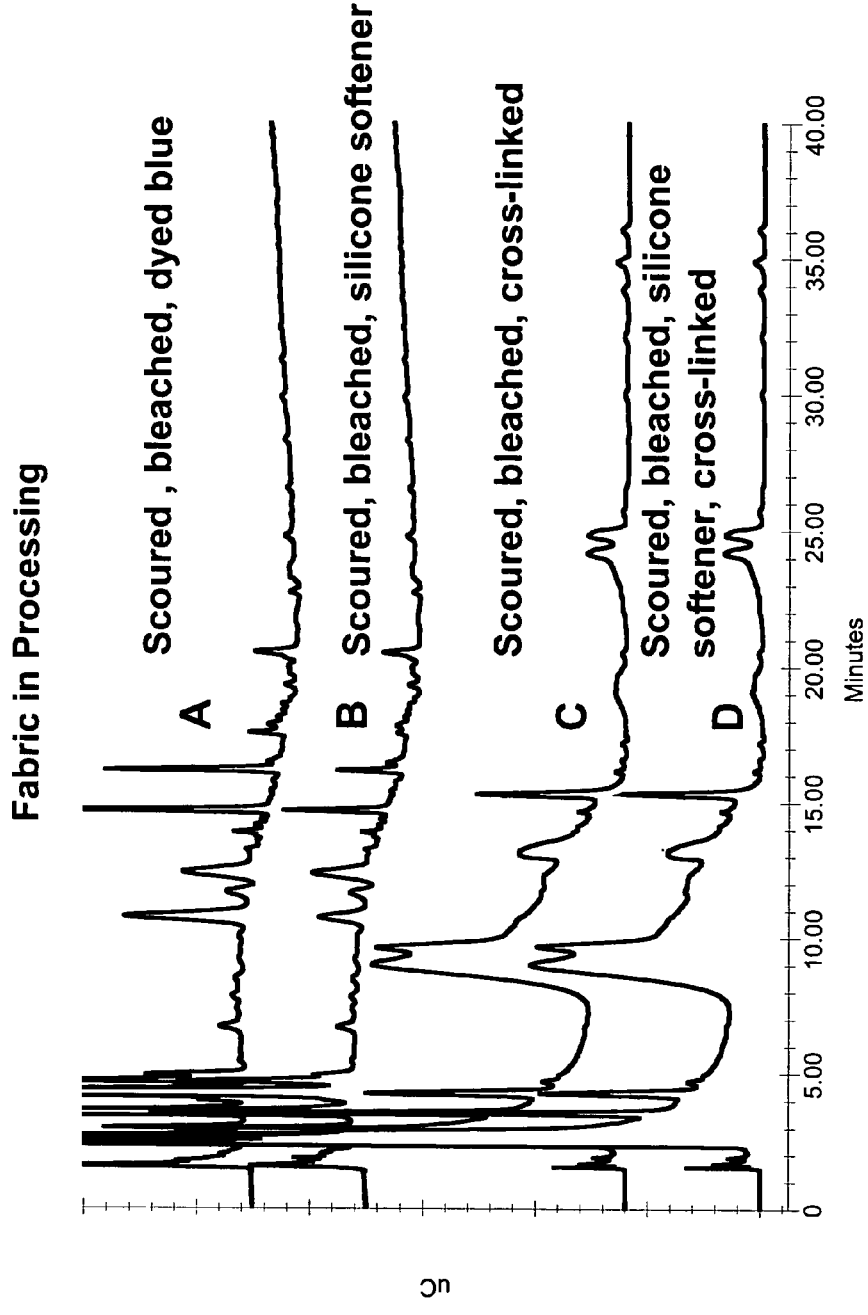
FIG. 9 shows multimers extracted from cotton fabrics at various stages of processing: a) scoured, bleached and blue dyed fabric; b) scoured, bleached with a silicone fabric softener; c) scoured, bleached and cross-linked; and d) scoured, bleached, and cross-linked with a silicone fabric softener.
Figure 10:
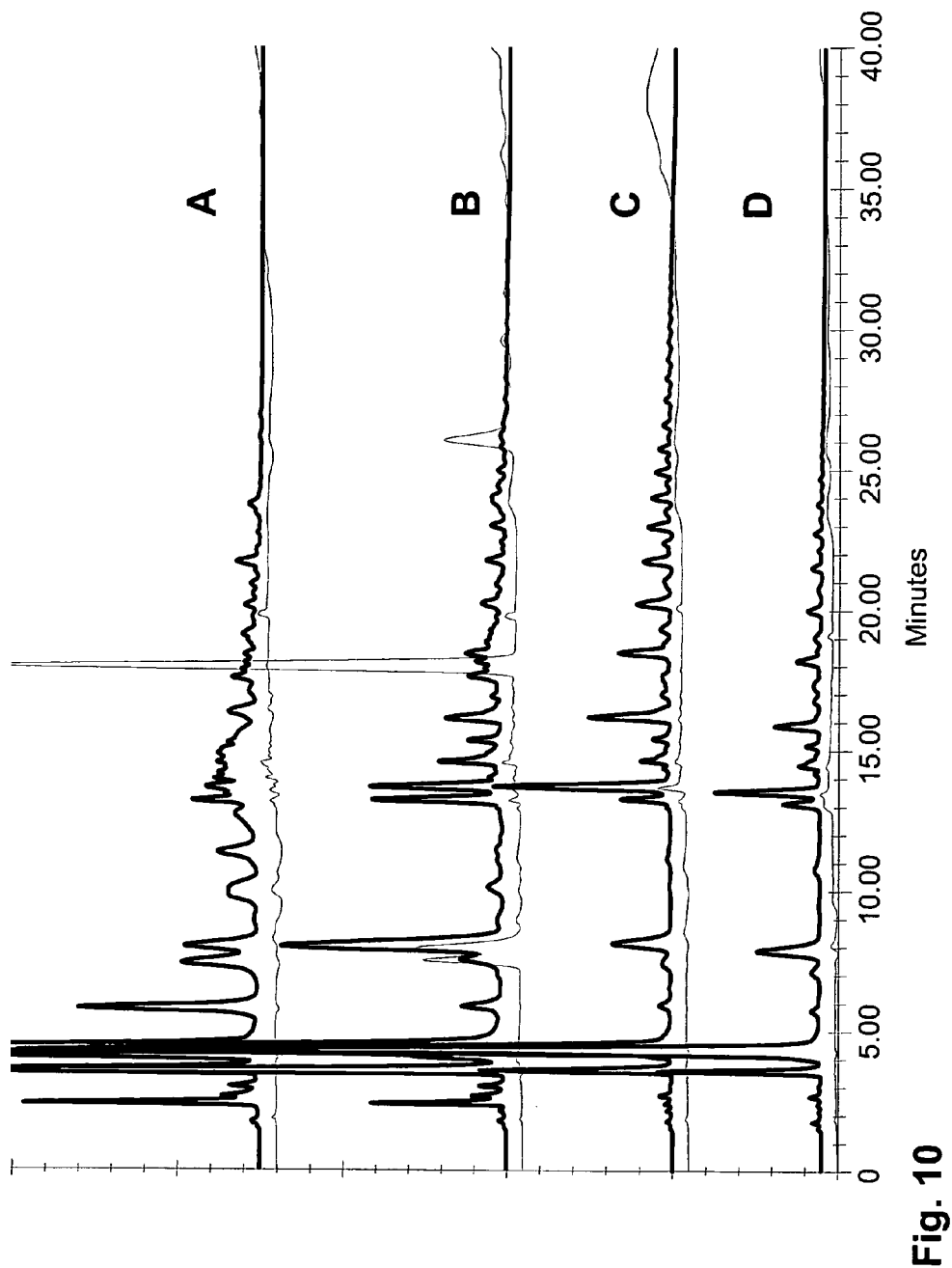
FIG. 10 shows multimers extracted from various paper products (matched on a weight basis): a) newsprint (light trace shows UV absorbance); b) Kraft paper corrugate (light trace shows UV absorbance—probably lignin); c) white card stock (light trace shows UV absorbance); and d) pink card stock (light trace shows UV absorbance).
Figure 11:
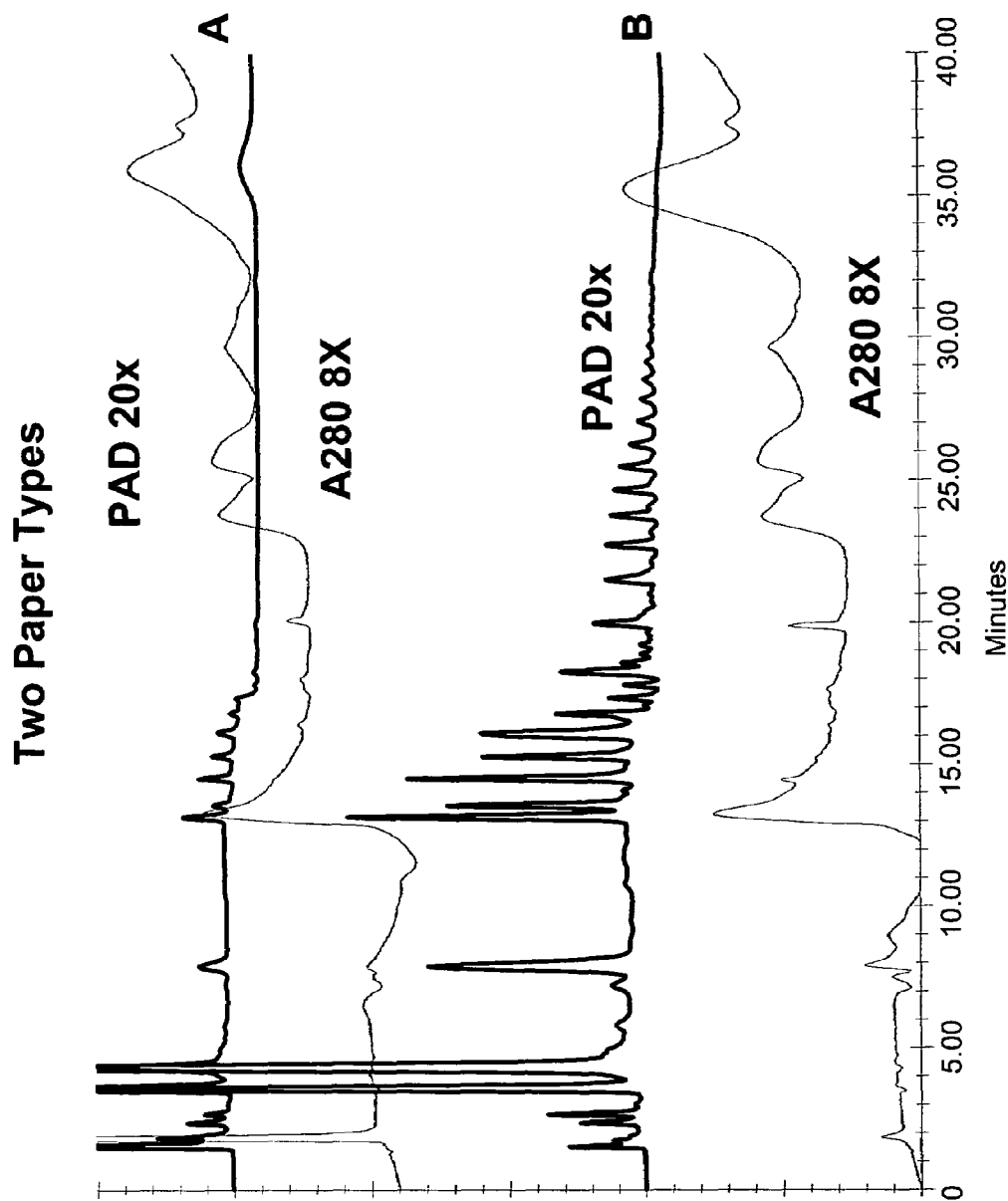
FIG. 11 shows a comparison (matched on a weight basis) of multimers extracted from two grades of "white" paper: a) shows a high purity bright white paper that shows relatively few multimers (light trace represents UV absorbance; b) shows a lower grade "copy" paper with a larger number of multimers (light trace is UV absorbance); the UV traces may be due in part to "optical brighteners" in the paper.

The method of the present invention has also been extended to pulp and paper products since they are derived from wood pulp. FIGS. 4, and 10-11 show the analyses of the following paper products: 25% cotton bond letterhead, newsprint, cardboard shipping box, a pink index card, white index card, catalogue paper, poster board, Xerox® MultiUse primary image paper and Hewlett-Packard® bright white inkjet paper. Again, it is evident that each type of paper product has a unique "signature" or "fingerprint" which probably reflects the pulp source and/or degree of processing. The most highly processed of the papers investigated appears to be the bright white inkjet paper (FIG. 11*a*) which shows the lowest abundance and distribution of the acid labile multimers. It is reasonable to assume that this paper has gone through more extensive washing and bleaching than the other papers analyzed.

The present invention would appear to be a more quantitative and automatic replacement for the "classical" microscopic approach of identifying wood samples. Previously a plant anatomist with considerable expertise was needed to identify small wood samples by examining microscopic cellular structures. There are a number of reasons that identification of wood samples might be required. In the case of imported wood products it might be required to demonstrate that none of the wood comes from endangered species. Some exotic wood is extremely expensive. Proof might be required that the wood is indeed of the correct, rare species. The present invention is also a quality control method for wood pulp processing. The type and quantity of multimers correlates with the degree of processing of wood pulp with the purer, higher quality pulps resulting from more extensive processing. The present method allows a given pulp sample to be rapidly and unambiguously evaluated to demonstrate pulp quality. This can be especially valuable in the formulation and quality control of material in recycled paper processing.

The oligomers utilized by the present invention appear to have a key role in the structure and synthesis of plant cell walls. The relative amounts of oligomers extracted from the developing fibers vary with age of the tissues. The period of greatest abundance of the lower molecular weight oligomers coincides with the time considered to be the onset of secondary cell wall synthesis. This correspondence suggests a role of the oligomers in the biosynthetic process. Such a role is also supported by the skewed distribution of the oligomers in the sequential bolls from the a plant stunted due to periodic drought stress. The roles of UDPG (uridine diphosphate glucose), sucrose and sucrose synthase have been well described (Delmer, 1999). Correlation between the levels of sucrose and the sucrosyl oligosaccharides and the cyclical changes in the relative quantities of the oligomers with the time of day is suggestive of a role for these sugars in the synthesis of the oligomers. The influence of the concentrations of myo-inositol, sucrose, raffinose, cellobiose and glycerol on the oligomers extracted from fibers following incubation also supports the notion that a number of these sugars may function as substrates. The prospect of substrates originating external to the fiber being incorporated into the cellulose of the fiber wall was first raised by Delmer, et. al. (Delmer, et. al, 1974).

The extraction of the carbohydrate-protein complex containing the oligomers is also suggestive of a biosynthetic role for the oligomers. The fact that this material can be isolated by filtration, but that it appears to be incorporated into a larger material which precipitates with increased incubation time is consistent with such a role. A likely scenario is that the rehydrated fibers are capable of carrying out some but not all of the enzymatic steps involved in the biosynthetic pathway. Alcoholic precipitation of the extracts provides a further fractionation step that allows one to readily view patterns in the extracted oligosaccharides that are otherwise obscured.

Clearly, biosynthesis of a polymer as large as cellulose may involve carbohydrates larger than sucrose. That such intermediates have not been described may be attributable to the complexity of carbohydrate biochemistry, and the relative fragility of glycoprotein associations, in the presence of rigorous extraction procedures. In this work, the use of mild extraction procedures, together with HPAEC-PAD, has revealed a number of, as yet not fully-characterized, oligomers. Such oligomers have been found in a number of cellulosic materials. The relative abundance of these oligomers varies with source and with developmental variables within a source. Moreover, the oligomers have been found in association with protein and, in certain experimental incubations, have behaved as if their solubility, acid-lability, and associated soluble products were affected by temperature and by amendment with biologically active saccharides. In short, they have behaved as if they were components of a biosynthetic apparatus. It is probable that the process of cellulose synthesis involves as yet un-described enzymatic activity, and that such activity is energetically favored by the conformation of glycan and glycoprotein conformations that are amenable to low-energy and possibly low-bioenergetic interconversion.

In addition to the equivalents of the claimed elements, obvious substitutions known to one with ordinary skill in the art are defined to be within the scope of the defined elements. The illustrated embodiment has been set forth only for the purposes of example and that should not be taken as limiting the invention. Therefore, it is to be understood that, within the scope of the appended claims, the invention may be practiced other than as specifically described herein.

REFERENCES

Amor, Y., Haigler, C. H., Johnson, S., Wainscott, M., and Delmer, D. P., 1995, A Membrane-Associated Form of Sucrose Synthase and Its Potential Role in Synthesis of Cellulose And Callose In Plants. Proc. Natl. Acad. Sci. USA 92:9353-9357.

Basra, A. S., Sarlach, R. S., Nayyar, H. and Malik, C. P., 1990, Sucrose Hydrolysis in Relation to Development Of Cotton (Gossypium Spp.) Fibres, Indian Journal of Experimental Biology, 28:958-988.

Brett, C. T., 2000, Cellulose Microfibrils in Plants: Biosynthesis, Deposition, and Integration into the Cell Wall, Int. Rev. Cytology 199:161-199.

Buchala, A., 1987, Acid β-fructofuranoside Fructohydrolase (Invertase) in Developing Cotton (*Gossypium arboreum* L.) Fibres and its Relationship to β-glucan Synthesis from Sucrose Fed to the Fibre Apopoplast, J. Plant. Physiol. 127:219-230.

Delmer, D. P., Beasley, C. A. and Ordin, L., 1974, Utilization of Nucleoside Diphosphate Gucoses in Developing Cotton Fibers, Plant Physiol. 53:149-153.

Delmer, D. P., 1999, Cellulose Biosynthesis: Exciting Times for a Difficult Field of Study. Ann. Rev. Plant Physiol. Plant Mol. Biol. 50:245-276.

Graves, D. A., and Stewart, J. McD., 1988, Analysis of the Protein Constituency of Developing Cotton Fibres, J. Exp. Botany 39:59-69.

Illingworth, B., Larner, J., and Cori, G. T. (1952) "Structure of Glycogens and Amylopectin: 1. Enzymatic Determination of Chain Length", J. Biol. Chem. 199: 631-640.

Manzi, A. E. And Varki, A., 1993, Compositional Analysis Of Glycoproteins, In Glycobiology: A Practical Approach, Eds. M. Fukuda And A. Kobata, Pp. 27-77, Oxford University Press.

Matthysse, A. G., Thomas, D. L., and White, A. R., 1995, Mechanism of Cellulose Synthesis in *Agrobacterium tumefaciens*, J. Bact. 117:1076-1081.

Meinert, M. C. and Delmer, D. P., 1977, Changes in Biochemical Composition of the Cell Wall of the Cotton Fiber During Development, Plant Physiol. 59, 1088-1097.

Mordoh, J., Krisman, C. H., and Leloir, L. F. (1966) "Further Studies on High Molecular Weight Liver Glycogen", Arch. Biochem. Biophys. 113; 265-272.

Morris, D. A. and Arthur, E. D., 1985, Invertase Activity, Carbohydrate Metabolism and Cell Expansion in the Stem of *Phaseolus vulgaris* L. J. Exptl. Bot. 36:623-633.

Murray, A. K. and Brown, J., 1997, Glycoconjugate Profiles of Developing fibers from Different Fruiting Branches on the Same Plant, 1997 Proceedings Beltwide Cotton Conferences, p. 1496-1499.

Murray, A. K., 1998, Method For Monitoring Growth And Detection Of Environmental Stress In Plants, U.S. Pat. No. 5,710,047.

Murray, A. K., 2000, Method For Detecting Growth And Stress In Plants, U.S. Pat. No. 6,051,435.

Murray, A. K. and Bandurski, R. S., 1975. Correlative Studies on Cell Wall Enzymes and Growth. *Plant Physiology* 56:143-147.

Murray, Allen K., Robert L. Nichols, and Gretchen F. Sassenrath-Cole, 2001, Cell Wall Biosynthesis: Glycan Containing Oligomers in Developing Cotton Fibers, Cotton Fabric, Wood and Paper, Phytochemistry, In Press.

Sturm, A. and Chrispeels, M. J., 1990, cDNA Cloning of Carrot Exocellular β-Fructofuranosidase and Its Expression in Response to Wounding and Bacterial Infection, The Plant Cell 2:1107-1119.

Sturm, A., Sebková, V., K., Lorenz, Hardegger, M., Lienhard, S., and Unger, C., 1995, Development- and organ-specific expression of the genes for sucrose synthase and three isoenzymes of acid β-frucdtofuranosidase in carrot, Planta 195:601-610.

Whistler, R. L. and BeMiller. J. N., 1958, Alkaline Degradation of Polysaccharides, Adv. Carbohydrate Chem. 13:289-329.

I claim:

1. A method of analyzing samples of polysaccharides or glycoprotein containing samples of plant or animal origin including textiles, wood pulp, cellulosic materials, starch, glycogen and plant products comprising the steps of: producing a cold water extract by extracting the samples with cold water; treating insoluble materials from the cold water extract step with dilute hot acid to yield an acid extract; neutralizing the acid extract; treating the neutralized acid extract with an alcohol to make an alcohol precipitate; redissolving the alcohol precipitate in an aqueous solution; and analyzing the aqueous solution to reveal a carbohydrate multimer.

2. A method of analyzing samples of polysaccharides or glycoprotein containing samples of plant or animal origin including textiles, wood pulp, cellulosic materials, starch, glycogen and plant products comprising the steps of: producing a cold water extract by extracting the samples with cold water; treating insoluble materials from the cold water extract step with dilute hot acid to yield an acid extract; neutralizing the acid extract; analyzing the aqueous solution to reveal a carbohydrate oligomers pattern and comparing to that of known reference standards.

3. The method of analyzing of claims 1 or 2, further comprising the step of analyzing soluble mono- and oligosaccharides contained in cold water extract comprising the steps of: producing a cold water extract by extracting the samples with cold water and comparing the relative distribution of individual mono- and oligosaccharides to that of known reference standards.

4. The method of analyzing of claim 1, wherein the alcohol used is selected from the group consisting of ethanol and 1-propanol.

5. The method of analyzing of claim 3, herein both ethanol and 1-propanol are used to make alcohol precipitates, and wherein the step of analyzing the aqueous solution compares redissolved ethanol precipitate to redissolved 1-propanol precipitate.

6. The method of analyzing of claim 1, wherein the redissolved alcohol precipitate is subjected to enzymatic digestion with a series of endoglycosidases and exoglycosidases prior to the step of analyzing, and wherein the results of different enzymatic digestions are compared in the step of analyzing.

7. The method of analyzing of claim 2, wherein the neutralized extract is subjected to enzymatic digestion with a series of endoglycosidases and exoglycosidases prior to the step of analyzing, and wherein the results of different enzymatic digestions are compared in the step of analyzing.

8. The method of analyzing claims 6 or 7, wherein the endoglycosidases are selected from the group consisting of endo .β-1,4-glucanase, exo-. α.-1,4-glucanase and α.-1-4-glucan glucohydrolase.

9. The method of analyzing of claims 1 or 2, wherein more heavily laundered textile samples are distinguished from less heavily laundered textile samples by a detection of fewer carbohydrate multimers, or quantitative differences or different relative abundance of glycan oligomers when the extract is analyzed.

10. The method of analyzing of claims 1 or 2, wherein the identity of the species of a sample of wood or other polysaccharide containing material of plant origin is determined and/or highly processed wood pulp is distinguished from less highly processed wood pulp by a difference in the relative quantity and distribution of carbohydrate multimers when the extract is analyzed and compared to appropriate reference samples.

11. The method of analyzing of claim 1, wherein a food grain is distinguished from other food grains by analyzing the aqueous extract and comparing the relative abundance of glycoconjugates in the extract to a similarly prepared extract of known samples of food grains.

12. A method of claims 1 or 2 wherein the sample is waste water and the sample is analyzed for the presence of glycan oligomers as evidence of discharge of polysaccharides from domestic laundry activities or other processing of polysaccharide containing material further comprising the step of analyzing the waste water sample directly and treating the waste water sample with dilute hot acid to yield an acid extract; neutralizing the acid extract; analyzing the aqueous solution to reveal a carbohydrate oligomer pattern and comparing the relative distribution of individual carbohydrate oligomers to that of known reference standards to determine the ultimate source of the polysaccharide material.

13. A method of claims 1 or 2 in which the sample contains a plant gum and the subsequent comparison of the glycan oligomer pattern with that of known samples of plant gums enables the identification of the plant gum in the unknown sample of food, pharmaceutical or work of art for the purpose of authenticating the work of art based on the plant gums known to have been used by the artist.

14. A method of identifying the source contribution of polysaccharides of plant or animal origin of dust in air by using the method of claims 1 or 2 on dust removed from an air sample by a filter to identify the polysaccharide based on the glycan oligomer distribution when compared with the glycan oligomer distribution pattern of a reference sample.

15. A method to identify differences due to environmental or genetic factors in alpha-glycans such as starch or glycogen using the method of claims 1 or 2 to identify the polysaccharide by comparing the relative distribution of glycan oligomers to the relative distribution of glycan oligomers in a similar extract of a reference sample.

* * * * *